United States Patent
Chokshi

(10) Patent No.: US 10,314,721 B2
(45) Date of Patent: Jun. 11, 2019

(54) INTERVERTEBRAL SPACERS

(71) Applicant: DeGen Medical, Inc., Florence, SC (US)

(72) Inventor: Rakesh P. Chokshi, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 0 days.

(21) Appl. No.: 15/654,900

(22) Filed: Jul. 20, 2017

(65) Prior Publication Data

US 2017/0312094 A1    Nov. 2, 2017

Related U.S. Application Data

(63) Continuation of application No. 14/680,566, filed on Apr. 7, 2015, now Pat. No. 9,757,248.

(60) Provisional application No. 62/114,860, filed on Feb. 11, 2015, provisional application No. 62/078,334, filed on Nov. 11, 2014, provisional application No. 61/976,792, filed on Apr. 8, 2014.

(51) Int. Cl.
*A61F 2/44*           (2006.01)

(52) U.S. Cl.
CPC ........ *A61F 2/447* (2013.01); *A61F 2/44* (2013.01); *A61F 2230/0082* (2013.01); *A61F 2230/0086* (2013.01); *A61F 2250/0026* (2013.01)

(58) Field of Classification Search
CPC .......... A61F 2/447; A61F 2002/4475; A61F 2/4455; A61F 2/4465
See application file for complete search history.

(56) References Cited

U.S. PATENT DOCUMENTS

| | | | |
|---|---|---|---|
| 5,961,554 | A | 10/1999 | Janson et al. |
| 5,980,572 | A | 11/1999 | Kim et al. |
| 6,558,424 | B2 | 5/2003 | Thalgott |
| 6,743,257 | B2 | 6/2004 | Castro |

(Continued)

FOREIGN PATENT DOCUMENTS

| | | |
|---|---|---|
| CN | 101049254 | 5/2010 |
| EP | 2025307 | 2/2009 |
| WO | WO2014028635 | 2/2014 |

OTHER PUBLICATIONS

AESCULAP Implant Systems, "CeSpaceXP Interbody System," p. 1, accessed Apr. 24, 2014, http://www.aesculapimplantsystems.com/default.aspx?pageid=3945.

(Continued)

*Primary Examiner* — Julianna N Harvey
(74) *Attorney, Agent, or Firm* — Buchanan Van Tuinen LLC

(57) ABSTRACT

Medical devices suitable for implantation in spaces between bones are described. An example medical device suitable for use as an intervertebral spacer includes a main body having an exterior proximal wall, an exterior distal wall, a first exterior lateral wall, a second exterior lateral wall, an upper surface, a lower surface, an interior proximal wall, an interior distal wall, a first interior lateral wall, a second interior lateral wall, and a longitudinal axis. The interior proximal wall, the interior distal wall, the first interior lateral wall, and the second interior lateral wall cooperatively define an interior cavity. The first and second exterior lateral walls are outwardly directed at an angle from the lower surface to the upper surface relative to the longitudinal axis.

20 Claims, 10 Drawing Sheets

(56) References Cited

U.S. PATENT DOCUMENTS

| | | | |
|---|---|---|---|
| 6,761,739 | B2 | 7/2004 | Shepard |
| 7,037,339 | B2 | 5/2006 | Houfburg |
| 7,137,997 | B2 | 11/2006 | Paul |
| 7,220,280 | B2 | 5/2007 | Kast et al. |
| 7,396,365 | B2 | 7/2008 | Michelson |
| D629,104 | S | 12/2010 | Calverley et al. |
| 7,875,080 | B2 | 1/2011 | Puno et al. |
| 8,328,872 | B2 | 12/2012 | Duffield et al. |
| 8,394,145 | B2 | 3/2013 | Weiman |
| D682,427 | S | 5/2013 | Farris et al. |
| 8,496,706 | B2 | 7/2013 | Ragab et al. |
| 8,496,713 | B2 | 7/2013 | Bennett et al. |
| 8,506,629 | B2 | 8/2013 | Weiland |
| 8,518,120 | B2 | 8/2013 | Glerum et al. |
| 8,523,910 | B2 | 9/2013 | Seifert et al. |
| 8,545,566 | B2 | 10/2013 | Niemiec et al. |
| 8,556,974 | B2 | 10/2013 | Suh et al. |
| 8,556,979 | B2 | 10/2013 | Glerum et al. |
| 8,597,355 | B2 | 12/2013 | Hansell |
| 8,597,359 | B2 | 12/2013 | Butler |
| 8,617,244 | B2 | 12/2013 | Reichen et al. |
| 8,632,593 | B2 | 1/2014 | Suh et al. |
| 8,641,768 | B2 | 2/2014 | Duffield et al. |
| 2004/0102850 | A1 | 5/2004 | Shepard |
| 2005/0149192 | A1 | 7/2005 | Zucherman et al. |
| 2007/0073400 | A1 | 3/2007 | Paul |
| 2007/0293948 | A1 | 12/2007 | Bagga et al. |
| 2009/0171461 | A1 | 7/2009 | Conner et al. |
| 2009/0198278 | A1 | 8/2009 | Shibata et al. |
| 2011/0160860 | A1 | 6/2011 | Johnston et al. |
| 2011/0172769 | A1* | 7/2011 | Ganem ............... A61F 2/30771 623/17.11 |
| 2011/0224796 | A1 | 9/2011 | Weiland et al. |
| 2012/0078370 | A1* | 3/2012 | James ..................... A61F 2/442 623/17.16 |
| 2012/0136443 | A1 | 5/2012 | Wenzel |
| 2012/0316649 | A1 | 12/2012 | Johnston et al. |
| 2013/0030544 | A1 | 1/2013 | Studer |
| 2013/0060339 | A1 | 3/2013 | Duffield et al. |
| 2013/0131726 | A1 | 5/2013 | Suh et al. |
| 2014/0012382 | A1 | 1/2014 | Doty |
| 2014/0052258 | A1* | 2/2014 | Ball ........................ A61F 2/442 623/17.16 |

OTHER PUBLICATIONS

Synthes Spine, "Advanced ACF Spacer: An allograft spacer with demineralized surfaces for anterior cervical interbody fusion," Synthes. com, 2004, pp. 1-7.

Lemke, Johannes, et al., "Polyetheretherketone (PEEK) Spacers for Anterior Cervical Fusion: A Retrospective Comparative Effectiveness Clinical Trial," Open Orthop. J. 2011; 5: 348-353.

Bonovo Orthopedics, "NuVasive PCM Cervical Disc," pp. 1-9, accessed Feb. 26, 2014, http://www.bonovo-ortho.com/Products/Spine(Cervical).php.

Depuy Spine, "Surgical Technique: VG2 Cervical Allograft," Brochure from Depuy Spine, Virginia Beach, VA, 2003.

Globus Medical, "Sustain & Sustain-R, Large, Trapezoidal thoracolumbar vertebral body replacement device," pp. 1-3, accessed Feb. 26, 2014, http://www.globusmedical.com/portfolio/sustain-sustain-r-large/.

Globus Medical, "Colonial, cervical interbody fusion device," pp. 1-2, accessed Feb. 26, 2014, http://globusmedical.com/portfolio/colonial/.

Globus Medical Inc. V. Depuy Synthes Products, LLC, Depuy Synthes Sales, Inc., Complaint, Case No. 1:13-cv-00854-UNA, at pp. 1-5 (D. Del. May 15, 2013).

Ho, Cheng, et al., "Kurokawa-type Laminoplasty using Hydroxyapatite Spacer for Cervical Myelopathy," Hong Kong J. Orthop. Surg. 2004: 8 (1):12-21.

Mahe Medical, "Perfect Spine, Vertebral Spacer System," from www.slideshare.net, slide No. 10, accessed Feb. 26, 2014, http://image.slidesharecdn.com/cages-130721071738-phpapp02/95/slide-10-638.jpg?cb=1374409152.

Niu, Chi-Chien et al., "Trapezoidal Titanium Cage in Anterior Cervical Interbody Fusion: A Clinical Experience," Chang Gung Med. J. Apr. 2005; 28 (4): 212-221.

Nutech Medical, "Interbody," Nutchmedical.com, pp. 1-3, accessed Feb. 26, 2014, http://nutechmedical.com/products/spine/interbody/.

United States Patent and Trademark Office, Office Action for U.S. Appl. No. 86/253,948, Applicant: DeGen Medical, Inc., dated Dec. 29, 2014.

Gelisim Medical, "Spinal Cerrahi", Gelisimmedikal.com, pp. 1-2, 2013, accessed Jun. 27, 2014, http://www.gelisimmedikal.com/eng/servical-peek-cage.asp.

European Patent Office, Extended European Search Report for Application No. 15162843.5, dated Jul. 5, 2016, pp. 1-6.

* cited by examiner

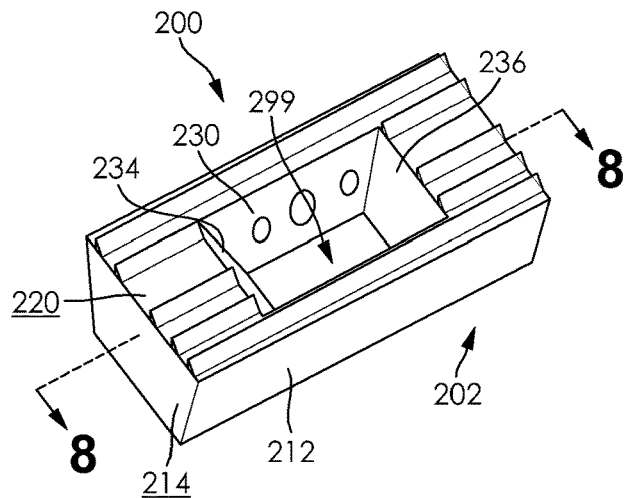
FIG. 7
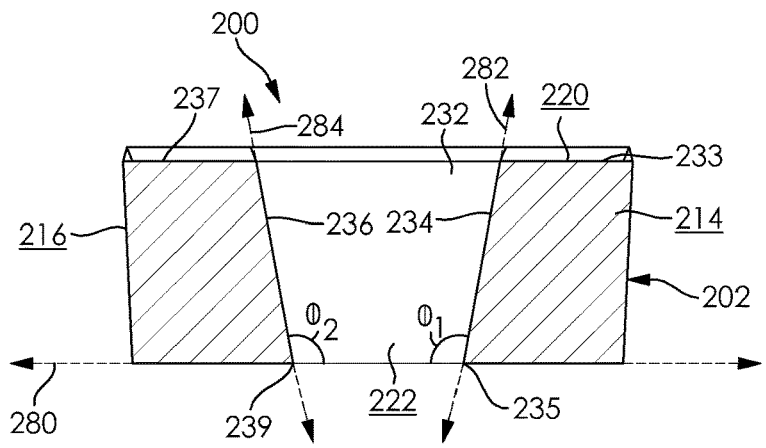
FIG. 8
FIG. 9

INTERVERTEBRAL SPACERS

RELATED APPLICATIONS

This application is a continuation of U.S. application Ser. No. 14/680,566, filed on Apr. 7, 2015 and which claims the benefit of U.S. Provisional Application No. 62/114,860, filed on Feb. 11, 2015, U.S. Provisional Application No. 62/078,334, filed on Nov. 11, 2014, and U.S. Provisional Application No. 61/976,792, filed on Apr. 8, 2014. Each of these related applications is hereby incorporated into this disclosure in its entirety.

FIELD

The disclosure relates generally to the field of implantable medical devices. More particularly, the disclosure relates to medical devices suitable for implantation in spaces between bones, such as in the spaces between vertebral bodies in a spinal column of a vertebrate. Specific examples relate to the field of intervertebral spacer medical devices.

BACKGROUND

Over time, bone may degenerate as a result of trauma, disease, and natural processes, such as aging. Bone degeneration can affect surrounding tissues and have a significant negative impact on the lifestyle of an animal. For example, destabilization of a spine in a vertebrate, such as a human being, may result in alteration of the spacing between adjacent vertebrae. This can place pressure on nerves that pass between the vertebral bodies. In turn, this pressure can cause pain, discomfort, and, eventually, nerve damage.

One way to alleviate the pain and discomfort that occurs after the degeneration or destabilization of a portion of the spine is to implant a medical device into the space between two adjacent vertebrae. Implanted in this manner, the medical device functions as a spacer that supports the structure of the spine by maintaining a desired spacing between the adjacent vertebrae.

One challenge in designing intervertebral spacers is developing a structure that achieves the desired spacing while avoiding displacement due to movement after implantation within the spinal column.

While the art provides several examples of intervertebral spacers, a need for improved medical devices remains.

BRIEF SUMMARY OF SELECTED EXAMPLES

Various example intervertebral spacers are described and illustrated herein.

An example intervertebral spacer comprises a main body having an exterior proximal wall, an exterior distal wall, a first exterior lateral wall, a second exterior lateral wall, an upper surface, a lower surface, an interior proximal wall, an interior distal wall, a first interior lateral wall, a second interior lateral wall, a longitudinal axis, and at least one stabilizing protrusion; the interior proximal wall is adjacent to each of the first interior lateral wall and the second interior lateral wall; the interior distal wall is adjacent to each of the first interior lateral wall and the second interior lateral wall; each of the interior proximal wall, the interior distal wall, the first interior lateral wall, and the second interior lateral wall extend from the upper surface to the lower surface; the interior proximal wall, the interior distal wall, the first interior lateral wall, and the second interior lateral wall cooperatively define an interior cavity; and the first exterior lateral wall is outwardly directed at an angle from the lower surface to the upper surface relative to the longitudinal axis.

Another example intervertebral spacer comprises a main body having an exterior proximal wall, an exterior distal wall, a first exterior lateral wall, a second exterior lateral wall, an upper surface, a lower surface, an interior proximal wall, an interior distal wall, a first interior lateral wall, a second interior lateral wall, a longitudinal axis, and at least one stabilizing protrusion; the interior proximal wall is adjacent to each of the first interior lateral wall and the second interior lateral wall; the interior distal wall is adjacent to each of the first interior lateral wall and the second interior lateral wall; each of the interior proximal wall, the interior distal wall, the first interior lateral wall, and the second interior lateral wall extend from the upper surface to the lower surface; the interior proximal wall, the interior distal wall, the first interior lateral wall, and the second interior lateral wall cooperatively define an interior cavity; the first exterior lateral wall is outwardly directed at an angle from the lower surface to the upper surface relative to the longitudinal axis; the first interior lateral wall is outwardly directed at an angle from the lower surface to the upper surface relative to the longitudinal axis; and the second interior lateral wall is outwardly directed at an angle from the lower surface to the upper surface relative to the longitudinal axis.

Another example intervertebral spacer comprises a main body having an exterior proximal wall, an exterior distal wall, a first exterior lateral wall, a second exterior lateral wall, an upper surface, a lower surface, an interior proximal wall, an interior distal wall, a first interior lateral wall, a second interior lateral wall, a longitudinal axis, and at least one stabilizing protrusion; the interior proximal wall is adjacent to each of the first interior lateral wall and the second interior lateral wall; the interior distal wall is adjacent to each of the first interior lateral wall and the second interior lateral wall; each of the interior proximal wall, the interior distal wall, the first interior lateral wall, and the second interior lateral wall extend from the upper surface to the lower surface; the interior proximal wall, the interior distal wall, the first interior lateral wall, and the second interior lateral wall cooperatively define an interior cavity; the first exterior lateral wall defines a first chamfered portion and a first groove; and the second exterior lateral wall defines a second chamfered portion and a second groove.

Another example intervertebral spacer comprises a main body having an exterior proximal wall, an exterior distal wall, a first exterior lateral wall, a second exterior lateral wall, an upper surface, a lower surface, an interior proximal wall, an interior distal wall, a first interior lateral wall, a second interior lateral wall, a longitudinal axis, and at least one stabilizing protrusion; the interior proximal wall is adjacent to each of the first interior lateral wall and the second interior lateral wall; the interior distal wall is adjacent to each of the first interior lateral wall and the second interior lateral wall; each of the interior proximal wall, the interior distal wall, the first interior lateral wall, and the second interior lateral wall extend from the upper surface to the lower surface; the interior proximal wall, the interior distal wall, the first interior lateral wall, and the second interior lateral wall cooperatively define an interior cavity; the first exterior lateral wall defines a first chamfered portion and a first groove; the second exterior lateral wall defines a second chamfered portion and a second groove; the exterior proximal wall and first exterior lateral wall cooperatively define a first connecting portion that defines a first S-curve;

and the exterior proximal wall and second exterior lateral wall cooperatively define a second connecting portion that defines a second S-curve.

Additional understanding of the claimed intervertebral spacers can be obtained by reviewing the detailed description of selected examples, below, with reference to the appended drawings.

BRIEF DESCRIPTION OF THE DRAWINGS

FIG. 7 is a perspective view of another example intervertebral spacer.

FIG. 8 is a cross-sectional view of the intervertebral spacer illustrated in FIG. 7, taken along line 8-8.

FIG. 9 is a perspective view of another intervertebral spacer.

DETAILED DESCRIPTION OF SELECTED EXAMPLES

Figure 1:
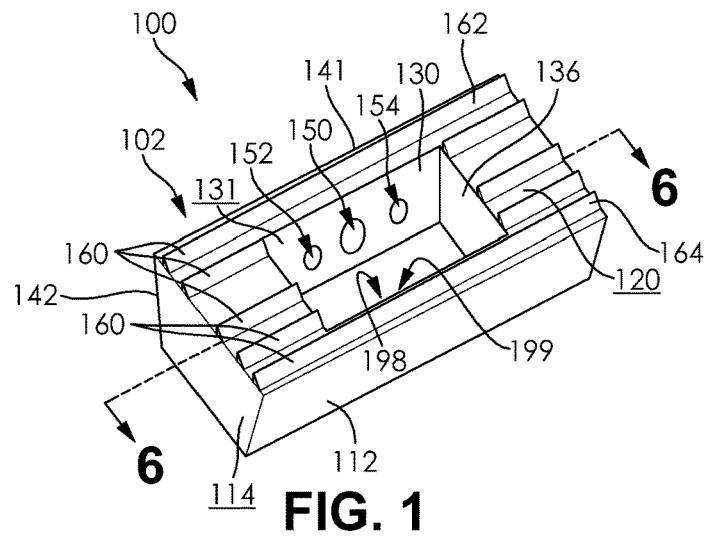
FIG. 1 is a perspective view of an example intervertebral spacer.

The following detailed description and the appended drawings describe and illustrate various example medical devices suitable for use as intervertebral spacers. The description and drawings are provided to enable one skilled in the art to make and use one or more example medical devices. They are not intended to limit the scope of the claims in any manner.

The medical devices described herein may be implanted within the spinal column of an animal, such as a human, to assist in maintaining support within the spinal column. The example intervertebral spacers described below are suitable for use within various intervertebral spaces along a spinal column. The intervertebral spacers are configured to be disposed between adjacent vertebrae of a spinal column.

As used herein, the term "horizontal axis" refers to an axis of an intervertebral spacer that extends horizontally through the center of the main body of the intervertebral spacer and through each of the first exterior lateral wall, the second exterior lateral wall, the first interior lateral wall, and the second interior lateral wall of the intervertebral spacer. A horizontal axis is perpendicular to the longitudinal axis of the intervertebral spacer.

As used herein, the term "vertical axis" refers to an axis of an intervertebral spacer that extends vertically through planes containing the lower and upper surfaces of the main body of the intervertebral spacer. A vertical axis is parallel to the longitudinal axis of the intervertebral spacer.

As used herein, the term "longitudinal axis" refers to the axis of an intervertebral spacer that extends vertically through planes containing the lower and upper surfaces of the main body and the geometric the center of the main body. The longitudinal axis is perpendicular to the individual plane containing each horizontal axis and is parallel to the individual plane containing each vertical axis.

As used herein, the term "cross-sectional shape" refers to the shape of a section of the main body that would be made by a plane cutting the main body transversely along a particular axis of the intervertebral spacer. For the purposes of this application, a cross-sectional shape will maintain the identity of the outermost outline of the portion of the main body to be cut along the axis. For example, were a plane to cut a cube-shaped main body defining a cylindrical interior cavity transversely along the horizontal axis, the cross-sectional shape of that particular main body would be considered square, even if the transverse cut left a corresponding circular gap in the aforementioned cross-section.

As used herein, the term "passageway" refers to a recess in a surface. The term does not require any particular cross-sectional shape. Non-limiting examples of passageway configurations include passageways having circular, triangular, square, rectangular, or trapezoidal cross-sectional shapes. The term also does not require any particular length relative to any other portion of the intervertebral spacer. For example, a passageway defined by an exterior proximal wall and an interior proximal wall may have any suitable length relative to the lengths of the exterior proximal wall and the interior proximal wall.

As used herein, the term "extension" refers a protrusion directed outwardly from the main body with respect to the longitudinal axis. The term does not require any particular cross-sectional shape. Non-limiting examples of cross-sectional shapes of an extension include circular, triangular, square, rectangular, and trapezoidal cross-sectional shapes. The term does not require any particular length or depth relative to any other portion of the intervertebral spacer. For example, an extension protruding from the exterior distal wall may have any suitable length and depth relative to the exterior distal wall.

FIGS. 1, 2, 3, 4A, 4B, 5, and 6 illustrate an example intervertebral spacer 100. The intervertebral spacer 100 comprises a main body 102 that defines an exterior proximal wall 110, an exterior distal wall 112, a first exterior lateral wall 114, a second exterior lateral wall 116, an interior proximal wall 130, an interior distal wall 132, a first interior lateral wall 134, a second interior lateral wall 136, an upper surface 120, a lower surface 122, and an inner cavity 199.

The exterior proximal wall 110 is adjacent the first exterior lateral wall 114 and the second exterior lateral wall 116. The exterior distal wall 112 is adjacent the first exterior lateral wall 114 and the second exterior lateral wall 116. Each of the exterior proximal wall 110, the exterior distal wall 112, the first exterior lateral wall 114, and the second exterior lateral wall 116 are adjacent each of the upper surface 120 and the lower surface 122.

As best illustrated in FIG. 1, the upper surface 120 has a generally rectangular shape and defines a generally rectangular cutout 198. Each of the upper surface 120 and the cutout 198 may, however, have other shapes. A skilled artisan will be able to determine a suitable shape for the upper surface and the cutout according to a particular example based on various considerations, including the position at which the intervertebral spacer will be implanted within the spinal column and the dimensions of the opening into which the intervertebral spacer will be implanted. Example suitable upper surface shapes include square, rounded rectangular, trapezoidal, and triangular. Example suitable cutout shapes include square, rounded rectangular, trapezoidal, and triangular. Additionally, the upper surface may be shaped the same as or differently than the cutout.

In the first example intervertebral spacer 100, the upper surface 120 defines protruding ridges 160 integrally formed with the main body 102 that are adapted to stabilize the intervertebral spacer 100 after implantation within a body. The protruding ridges 160 are generally pyramidal in shape. The main body 102 defines five protruding ridges 160, including a first protruding ridge 162 and a fifth protruding ridge 164. The first and fifth protruding ridges 162, 164 respectively define first and fifth ridge tips 163, 165. In other embodiments, the upper surface may define more than or less than five protruding ridges. The protruding ridges 160 may be integrally formed with the main body 102, as illustrated in the Figures, or can comprise one or more separate members directly or indirectly attached to the main body via adhesives, welding, a mechanical connector, or another suitable attachment mechanism in other embodiments. A skilled artisan will be able to determine suitable sizes and shapes of the protruding ridges according to a particular example based on various considerations, including the position at which the intervertebral spacer will be implanted within the spinal column and the dimensions of the opening into which the intervertebral spacer will be implanted. Examples of other suitable structures that may be used in place of protruding ridges include indented surfaces, protruding ribs, and wave-like structures having pointed apexes and rounded valleys. Any individual protruding ridge may be shaped the same as or differently than any other individual protruding ridge in other embodiments.

In the first example intervertebral spacer 100, the first ridge tip 163 is disposed on a plane 170 that is parallel to a horizontal axis (not illustrated in the Figures). The fifth ridge tip 165 is disposed on a second plane 172 that forms an upper surface angle $\beta_1$ with respect to the first plane 170 on which the first ridge tip 163 lies. The intervertebral spacer may define any suitable upper surface angle $\beta_1$. A skilled artisan will be able to determine a suitable upper surface angle for the intervertebral spacer according to a particular example based on various considerations, including the position at which the intervertebral spacer will be implanted within the spinal column and the dimensions of the opening into which the intervertebral spacer will be implanted. Examples of suitable upper surface angles include angles between about 0° and about 10°, angles between about 2° and about 8°, and angles between about 4° and about 6°.

Figure 5:
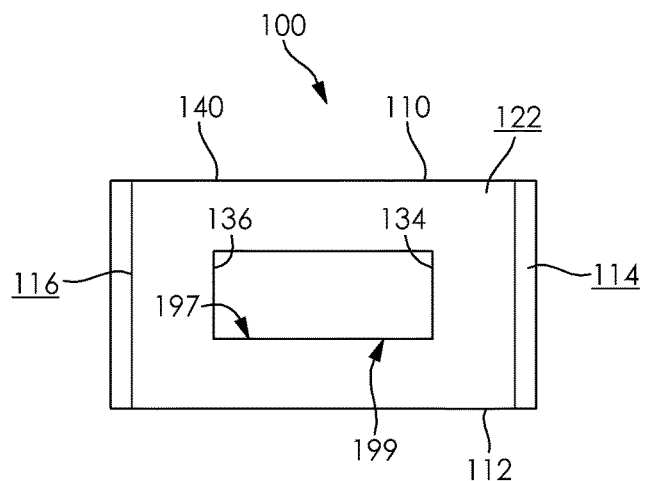
FIG. 5 is a bottom view of the intervertebral spacer illustrated in FIG. 1.
Figure 6:
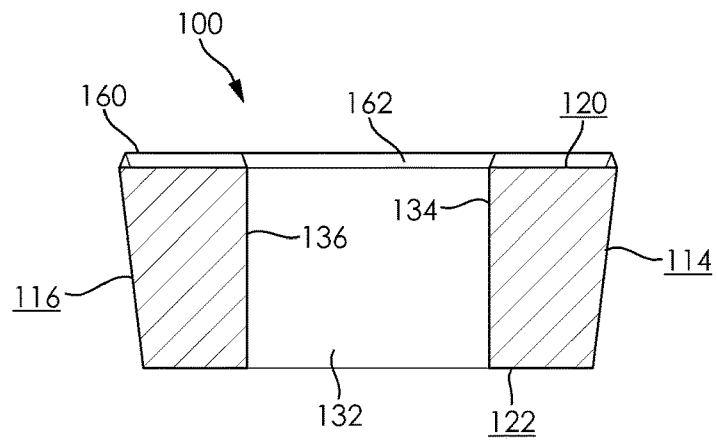
FIG. 6 is a cross-sectional view of the intervertebral spacer illustrated in FIG. 1, taken along line 6-6.

As best illustrated in FIG. 5, the lower surface 122 has a generally rectangular shape and defines a generally rectangular cutout 197. Each of the lower surface 122 and cutout 197 may, however, have other shapes. A skilled artisan will be able to determine a suitable shape for the lower surface and the cutout according to a particular example based on various considerations, including the position at which the intervertebral spacer will be implanted within the spinal column and the dimensions of the opening into which the intervertebral spacer will be implanted. Example suitable lower surface shapes include square, rounded rectangular, trapezoidal, and triangular. Example suitable cutout shapes include square, rounded rectangular, trapezoidal, and triangular. Additionally, the lower surface may be shaped differently than the cutout.

Figure 2:
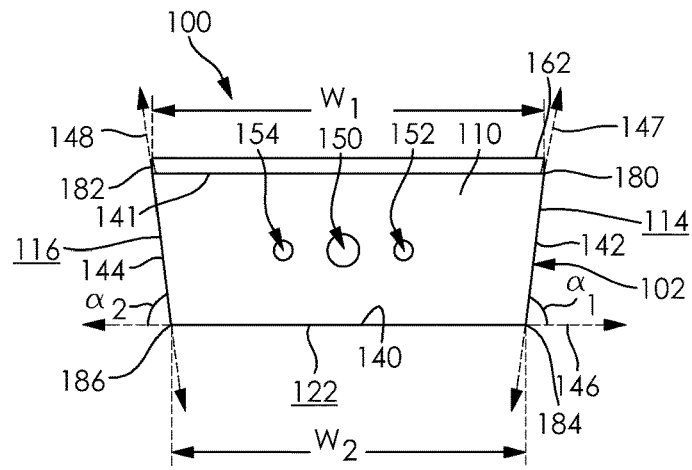
FIG. 2 is an end view of the intervertebral spacer illustrated in FIG. 1.
Figure 3:
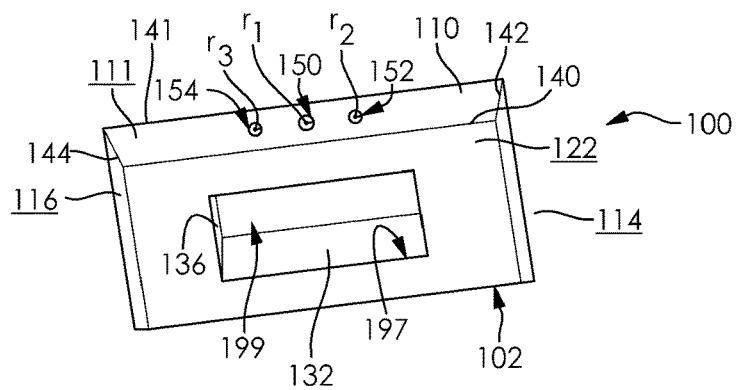
FIG. 3 is another perspective view of the intervertebral spacer illustrated in FIG. 1.
Figures 4A, 4B:
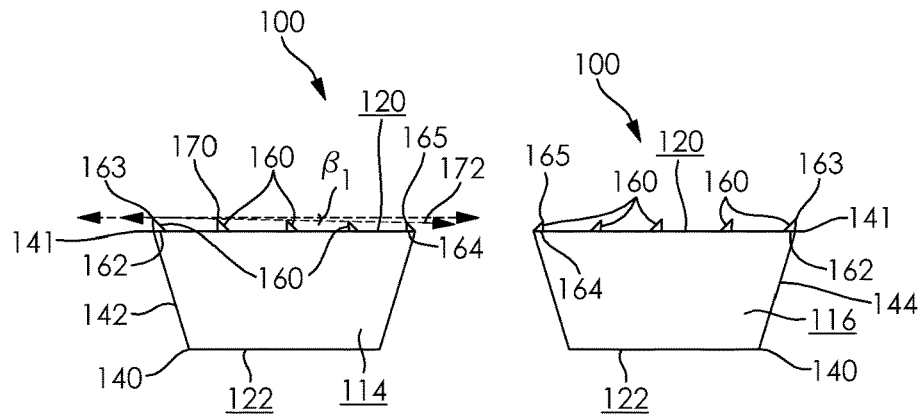
FIG. 4A is a first side view of the intervertebral spacer illustrated in FIG. 1.
FIG. 4B is a second side view of the intervertebral spacer illustrated in FIG. 1.

FIG. 2 best illustrates the exterior proximal wall 110. The exterior proximal wall 110 is disposed on a plane (not illustrated in the Figures) that is parallel to the longitudinal axis (not illustrated in the Figures); the plane on which the proximal wall 110 is disposed is also parallel to the plane (not illustrated in the Figures) on which the exterior distal wall 112 is disposed. The exterior proximal wall 110, furthermore, comprises a lower edge 140 that is adjacent the lower surface 122, an upper edge 141 that is adjacent the upper surface 120, a first lateral edge 142 that is adjacent the first exterior lateral wall 114, and a second lateral edge 144 that is adjacent the second exterior lateral wall 116. The lower edge 140 is disposed on a third plane 146 that is parallel to a horizontal axis (not illustrated in the Figures). The first and second lateral edges 142, 144 are disposed on fourth and fifth planes 147, 148, respectively. The fourth plane 147 forms a first lateral angle $\alpha_1$ with the third plane 146; the fifth plane 148 forms a second lateral angle $\alpha_2$ with respect to the third plane 146. The first and second lateral angles $\alpha_1$, $\alpha_2$ may have any angular measurement. A skilled artisan will be able to determine suitable first and second lateral angles for the exterior proximal wall according to a particular example based on various considerations, including the position at which the intervertebral spacer will be implanted within the spinal column and the dimensions of the opening into which the intervertebral spacer will be implanted. Examples of suitable first lateral angles include angles between about 60° and about 85°, angles between about 70° and about 80°, and angles between about 73° and about 77°. Examples of suitable second lateral angles include angles between about −60° and about −85°, angles between about −70° and about −80°, and angles between about −73° and about −77°. Furthermore, the first lateral angle may be equal to, substantially equal to, or non-equal to the second lateral angle.

The exterior proximal wall 110 also defines first and second widths $w_1$, $w_2$. The first width $w_1$ extends from a first point 180, which is disposed where the upper edge 141 is adjacent the first lateral edge 142, to a second point 182, which is disposed where the upper edge 141 is adjacent the second lateral edge 144. The second width $w_2$ extends from a third point 184, which is disposed where the lower edge 140 is adjacent the first lateral edge 142, to a fourth point 186, which is disposed where the lower edge 140 is adjacent the second lateral edge 144. In the illustrated embodiment, the first width $w_1$ is greater than the second width $w_2$; however, each of the first and second widths $w_1$, $w_2$ can have any suitable dimension. A skilled artisan will be able to determine suitable first and second widths for the exterior proximal wall according to a particular example based on various considerations, including the position at which the intervertebral spacer will be implanted within the spinal column and the dimensions of the opening into which the intervertebral spacer will be implanted. Example suitable first widths include widths between about 10 millimeters (hereinafter, "mm") and about 30 mm, widths between about 14 mm and about 26 mm, and widths between about 18 mm and about 22 mm. Example suitable second widths include widths between about 10 mm and about 20 mm, widths between about 12 mm and about 18 mm, and widths between about 14 mm and about 16 mm. Furthermore, the first width may be greater than, equal to, about equal to, or less than the second width.

The interior proximal wall 130 is adjacent the first interior lateral wall 134 and the second interior lateral wall 136. The interior distal wall 132 is adjacent the first interior lateral wall 134 and the second interior lateral wall 136. Each of the interior proximal wall 130, the interior distal wall 132, the first interior lateral wall 134, and the second interior lateral wall 136 are adjacent each of the upper surface 120 and the lower surface 122 of the main body 102. Furthermore, the interior proximal wall 130, the interior distal wall 132, the first interior lateral wall 134, and the second interior lateral wall 136 cooperatively define an interior cavity 199.

In the illustrated embodiment, each of the interior proximal wall 130, the interior distal wall 132, the first interior lateral wall 134, and the second interior lateral wall 136 are parallel to the longitudinal axis. The interior proximal wall 130 is orthogonal to each of the first interior lateral wall 134 and the second interior lateral wall 136, and the interior distal wall 132 is orthogonal to each of the first interior lateral wall 134 and the second interior lateral wall 136. Each of the interior proximal wall, interior distal wall, and first and second interior lateral walls may be disposed it any angle with respect to the longitudinal axis, however. A skilled artisan will be able to determine how to dispose the interior proximal wall, the interior distal wall, and the first and second interior lateral walls with respect to the longitudinal axis according to a particular example based on various considerations including the position at which the intervertebral spacer will be implanted within the spinal column and the dimensions of the opening into which the intervertebral spacer will be implanted. In an alternative embodiment, the interior distal wall may be disposed on a first plane that is set at an angle with respect to the longitudinal axis. In another embodiment, one or both of the first and second interior lateral walls may be disposed on second and third planes that are set at an angle with respect to the longitudinal axis. In a different embodiment, the interior distal wall may be disposed on a fourth plane that is set at an angle with respect to the longitudinal axis.

In the first example intervertebral spacer 100, the exterior proximal wall 110 and interior proximal wall 130 cooperatively define a middle passageway 150, a first outer passageway 152, and a second outer passageway 154. Each of the middle passageway 150, the first outer passageway 152, and the second outer passageway 154 extend from the surface 111 of the exterior proximal wall 110 to the surface 131 of the interior proximal wall 130. The middle passageway 150 defines a first radius $r_1$; the first outer passageway 152 and the second outer passageway 154 define second and third radii $r_2$, $r_3$, respectively. The middle, first outer, and second outer passageways 150, 152, 154 can have any suitable radii $r_1$, $r_2$, $r_3$, respectively. A skilled artisan will be able to determine suitable first, second, and third radii for the middle, first outer, and second outer passageways, respectively, based on various considerations, including the position at which the intervertebral spacer will be implanted within the spinal column and the dimensions of the opening into which the intervertebral spacer will be implanted. Examples of a suitable first radius includes a radius between about 2 mm and about 8 mm and a radius between about 4 mm and about 6 mm. Examples of suitable second and third radii include radii between about 1 mm and about 4 mm and about 2 mm and about 3 mm. Furthermore, the first radius may be equal to, substantially equal to, or non-equal to the second and third radii. Moreover, the second radius may be equal to, substantially equal to, or non-equal to the third radius.

FIGS. 7 and 8 illustrate a second example intervertebral spacer 200. This intervertebral spacer 200 is similar to the intervertebral spacer 100 shown in FIGS. 1, 2, 3, 4A, 4B, 5, and 6, except as detailed below. Thus, the intervertebral spacer 200 comprises a main body 202 that defines an exterior proximal wall (not illustrated in the Figures), an exterior distal wall 212, a first exterior lateral wall 214, a second exterior lateral wall 216, an interior proximal wall 230, an interior distal wall 232, a first interior lateral wall 234, a second interior lateral wall 236, an upper surface 220, a lower surface 222, and an interior cavity 299.

The first interior lateral wall 234 extends from a first point 233 disposed adjacent the upper surface 220 to a second point 235 disposed adjacent the lower surface 222. The second point 235 is disposed on a first plane 280 that is perpendicular to the longitudinal axis (not illustrated in the Figures). The first interior lateral wall 234 is disposed on a second plane 282 that forms a first interior outward angle $\phi_1$ relative to the first plane 280. Additionally, the second interior lateral wall 236 extends from a third point 237 disposed adjacent the upper surface 220 to a fourth point 239 disposed adjacent the lower surface 222. The fourth point 239 is disposed on the first plane 280. The second interior lateral wall 236 is disposed on a third plane 284 that forms a second interior outward angle $\phi_2$ relative to the first plane 280. The first and second interior lateral walls 234, 236 can define any first and second interior outward angles $\phi_1$, $\phi_2$. A skilled artisan will be able to determine appropriate first and second interior outward angles according to a particular embodiment based on various considerations, including the position at which the intervertebral spacer will be implanted within the spinal column and the dimensions of the opening into which the intervertebral spacer will be implanted. Examples of suitable first interior outward angles include angles between about 90° and about 125°, angles between about 98° and about 117°, and angles between about 104° and about 111°. Examples of suitable second interior outward angles include angles between about −90° and about −125°, angles between about −98° and about −117°, and angles between about −104° and about −111°. Additionally, the first interior outward angle may be greater than, equal to, or less than the second interior outward angle.

Figure 10:
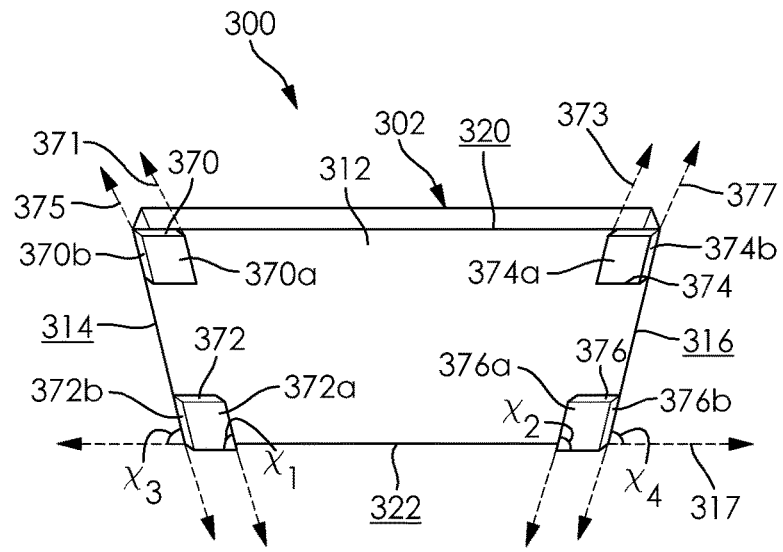
FIG. 10 is an end view of the intervertebral spacer illustrated in FIG. 9.
Figure 11A:
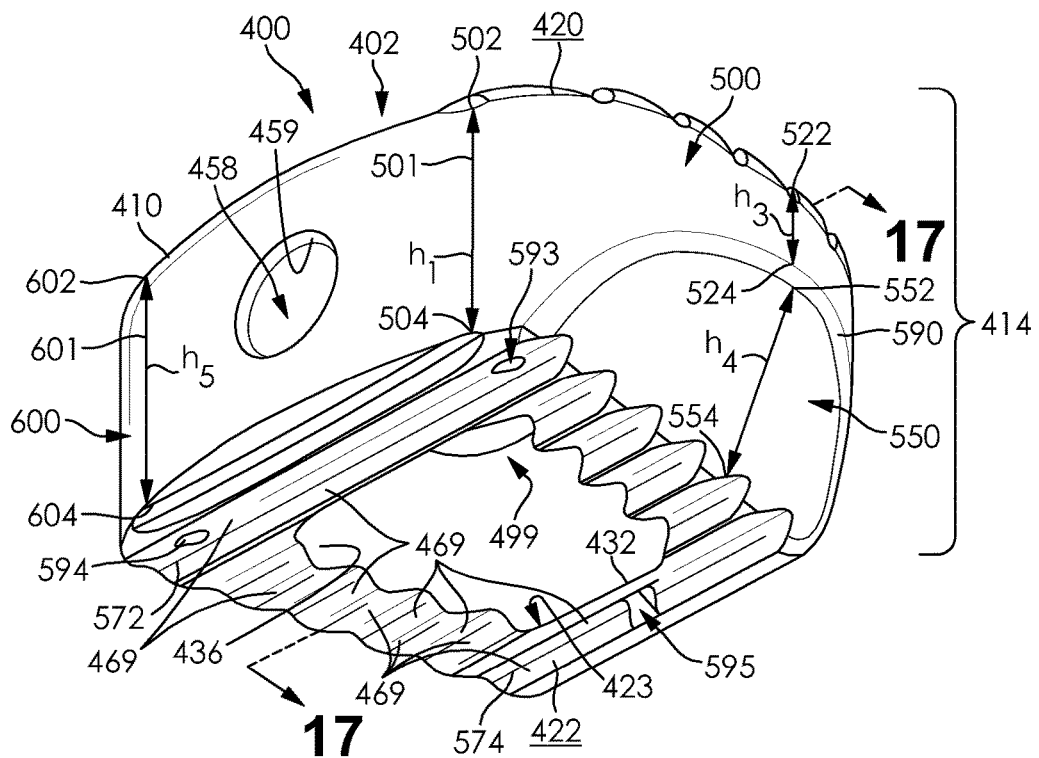
FIG. 11A is a perspective view of another intervertebral spacer.
Figure 11B:
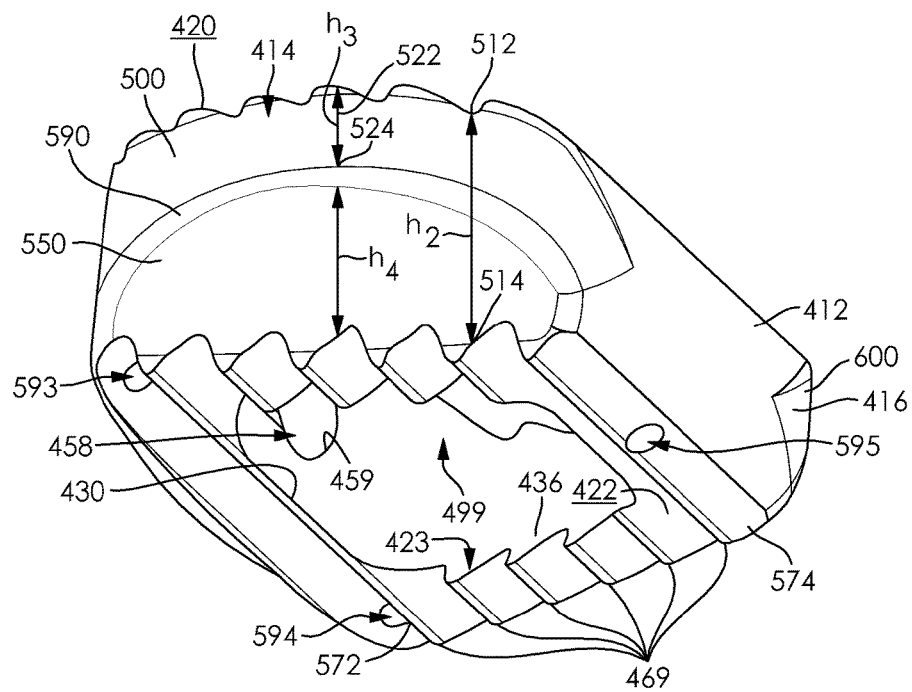
FIG. 11B is another perspective view of the intervertebral spacer illustrated in FIG. 11A.
Figure 12A:
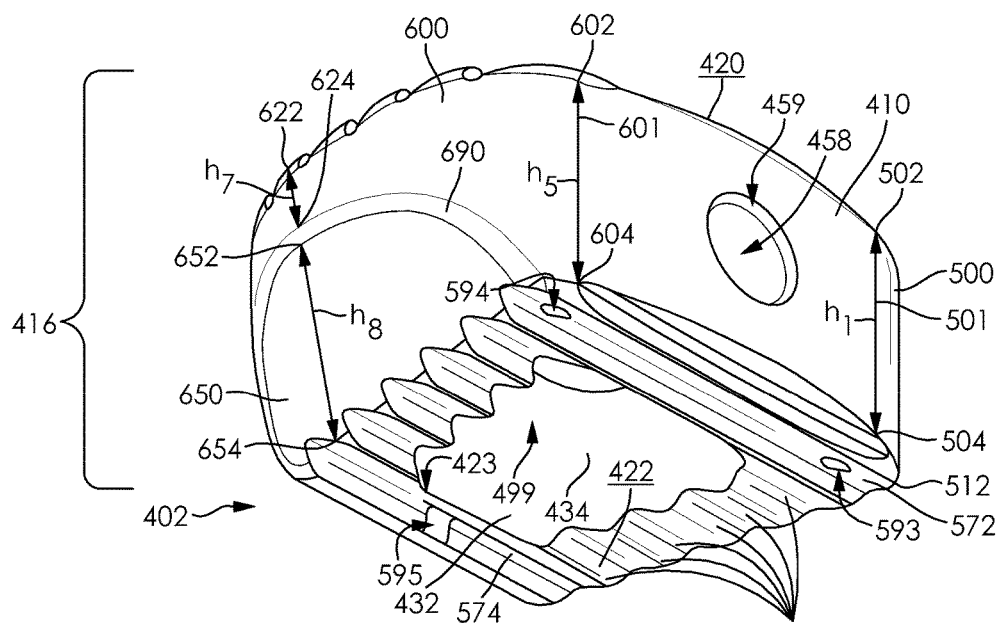
FIG. 12A is another perspective view of the intervertebral spacer illustrated in FIG. 11A.
Figure 12B:
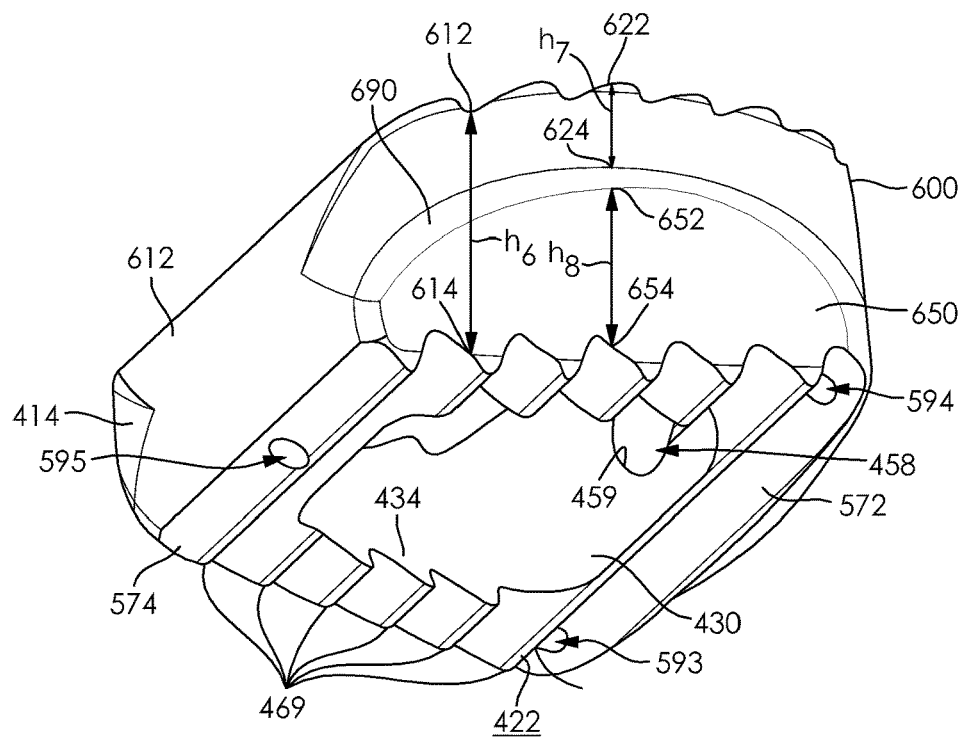
FIG. 12B is another perspective view of the intervertebral spacer illustrated in FIG. 11A.

FIGS. 9 and 10 illustrate a third example intervertebral spacer 300. This intervertebral spacer 300 is similar to the intervertebral spacer 200 shown in FIGS. 7 and 8, except as detailed below. Thus, the intervertebral spacer 300 comprises a main body 302 that defines an exterior proximal wall (not illustrated in the Figures), an exterior distal wall 312, a first exterior lateral wall 314, a second exterior lateral wall 316, an interior proximal wall 330, an interior distal wall (not illustrated in the Figures), a first interior lateral wall 334, a second interior lateral wall 336, an upper surface 320, a lower surface 322, and an interior cavity 399.

In this embodiment, the exterior distal wall 312 has first, second, third, and fourth extensions 370, 372, 374, 376 (hereinafter, collectively referred to as "the four extensions 370, 372, 374, 376") configured to engage uncovertebral joints (not illustrated in the Figures) and extend into the spaces surrounding the uncovertebral joints (not illustrated in the Figures).

Each of the four extensions 370, 372, 374, 376 is a quadrilateral. Each of the four extensions 370, 372, 374, 376 can have any suitable shape, however. A skilled artisan will be able to determine a suitable shape for each of the four extensions and a suitable number of extensions according to a particular example based on various considerations including the position at which the intervertebral spacer will be implanted within the spinal column and the dimensions of the opening into which the intervertebral spacer will be implanted. Examples of suitable shapes of the four extensions include square, trapezoidal, triangular, circular, and rectangular. Further, any one of the four extensions may have a different shape than any other one of the four extensions. Additionally, in alternative embodiments, the exterior distal wall may have zero, one, two, three, five, or more than five extensions.

The first extension 370 is disposed adjacent the upper surface 320 and the first exterior lateral wall 314 on the exterior distal wall 312. The second extension 372 is disposed adjacent the lower surface 322 and the first exterior lateral wall 314 on the exterior distal wall 312. The third extension 374 is disposed adjacent the upper surface 320 and the second exterior lateral wall 316 on the exterior distal wall 312. The fourth extension 376 is disposed adjacent the lower surface 322 and the second exterior lateral wall 316 on the exterior distal wall 312. However, each of the four extensions 370, 372, 374, 376 may be disposed anywhere on the exterior distal wall 312. A skilled artisan will be able to determine how best to position the four extensions based on various considerations, including the position at which the intervertebral spacer will be implanted within the spinal column and the dimensions of the opening into which the intervertebral spacer will be implanted. In other embodiments, the extensions may be disposed anywhere on the exterior distal wall.

The first extension 370 defines a first inner edge 370a and a first outer edge 370b. The second extension 372 defines a second inner edge 372a and a second outer edge 372b. The third extension 374 defines a third inner edge 374a and a third outer edge 374b. The fourth extension 376 defines a fourth inner edge 376a and a fourth outer edge 376b. Each of the first and second inner edges 370a, 372a is disposed on a first inner plane 371 that forms a first interior extension angle $\chi_1$ with respect to the plane 317 on which the lower surface 322 is disposed. Each of the third and fourth inner edges 374a, 376a is disposed on a second inner plane 373 that forms a second interior extension angle $\chi_2$ with respect to the plane 317 on which the lower surface 322 is disposed. Each of the first and second outer edges 370b, 372b is disposed on a first outer plane 375 that forms a first exterior extension angle $\chi_3$ with respect to the plane 317 on which the lower surface 322 is disposed. Each of the third and fourth outer edges 374b, 376b is disposed on a second outer plane 377 that forms a second exterior extension angle $\chi_4$ with respect to the plane 317 on which the lower surface 322 is disposed. The main body 302 may define any first and second interior extension angles $\chi_1$, $\chi_2$ and first and second exterior extension angles $\chi_3$, $\chi_4$. A skilled artisan will be able to determine suitable first and second interior extension angles and first and second exterior extension angles according to a particular embodiment based on various considerations including the position at which the intervertebral spacer will be implanted within the spinal column and the dimensions of the opening into which the intervertebral spacer will be implanted. Examples of suitable first interior extension angles include angles between about 35° and 55° and angles between about 42° and about 48°. Examples of suitable second interior extension angles include angles between about −35° and about −55° and angles between about −42° and about −48°. Examples of suitable first exterior extension angles include angles between about 20° and about 40° and angles between about 27° and about 33°. Examples of suitable second exterior extension angles include angles between about −20° and about −40° and angles between about −27° and about −33°. In various alternatives, the first interior extension angle may be greater than, equal to, or less than the angular measurement of the second interior extension angle. In other alternatives, the first exterior extension angle may be greater than, equal to, or less than the angular measurement of the second exterior extension angle.

FIGS. 11A, 11B, 12A, 12B, 13, 14, 15, 16, and 17 illustrate another example intervertebral spacer 400. This intervertebral spacer 400 is similar to the intervertebral spacer 200 shown in FIGS. 7 and 8, except as detailed below. Thus, the intervertebral spacer 400 comprises a main body 402 that defines an exterior proximal wall 410, an exterior distal wall 412, a first exterior lateral wall 414, a second exterior lateral wall 416, an interior proximal wall 430, an interior distal wall 432, a first interior lateral wall 434, a second interior lateral wall 436, an upper surface 420, a lower surface 422, and an interior cavity 499.

In this embodiment, the upper surface 420 is generally rounded trapezoidal in shape and defines a generally rounded trapezoidal cutout 421. The upper surface 420 defines a first edge 490 at which the upper surface 420 is adjacent the exterior proximal wall 410 and each of the first and second exterior lateral walls 414, 416. The first edge 490 defines a first width $w_1$ extending from a first point 491 disposed on the first edge 490 to a second point 492 disposed on the first edge 490. The first and second points 491, 492 are disposed on the first edge 490 such that they are adjacent the first and second exterior lateral walls 414, 416, respectively. The upper surface 420 also defines a second edge 494 at which the upper surface 420 is adjacent the interior proximal wall 430 and each of the first and second interior lateral walls 434, 436. The second edge 494 defines a second width $w_2$ extending from a third point 495 disposed on the second edge 494 to a fourth point 496 disposed on the second edge 494. The third and fourth points 495, 496 are disposed on the second edge 494 such that they are adjacent the first and second interior lateral walls 434, 436, respectively. Furthermore, the upper surface 420 defines a third edge 497 at which the upper surface 420 is adjacent the interior distal wall 432 and each of the first and second interior lateral walls 434, 436. The third edge 497 defines a third width $w_3$ extending from a fifth point 498 disposed on the third edge 497 to a sixth point 591 disposed on the third edge 497. The fifth and sixth points 498, 591 are disposed on the third edge 497 such that they are adjacent the first and second interior lateral walls 434, 436, respectively. The upper surface 420 also defines a fourth edge 487 at which the upper surface 420 is adjacent the exterior distal wall 412 and each of the first and second exterior lateral walls 414, 416. The fourth edge 487 defines a fourth width $w_4$ extending from a seventh point 488 disposed on the fourth edge 487 to an eighth point 489 disposed on the fourth edge 487. The seventh and eighth points 488, 489 are disposed on the fourth edge 487 such that they are adjacent the first and second exterior lateral walls 414, 416, respectively. The upper surface 420 further defines a continuous perimeter 599 that extends around the entire upper surface 420 and, at various points, is adjacent the exterior proximal wall 410, exterior distal wall 412, first exterior lateral wall 414, and second exterior lateral wall 416. The continuous perimeter 599 has a perimeter length p, described below.

In the illustrated embodiment, the first width $w_1$ is greater than the second width $w_2$, the second width $w_2$ is greater than the fourth width $w_4$, and the fourth width $w_4$ is greater than the third width $w_3$. However, an individual first, second, third, or fourth width $w_1$, $w_2$, $w_3$, $w_4$ may be greater than, equal to, about equal to, or less than any other individual first, second, third, or fourth width $w_1$, $w_2$, $w_3$, $w_4$. The upper surface can define any suitable first, second, third, and fourth widths in other embodiments. A skilled artisan will be able to select appropriate first, second, third, and fourth widths according to a particular embodiment based on various considerations, including the position at which the intervertebral spacer will be implanted within the spinal column and the dimensions of the opening into which the intervertebral spacer will be implanted. Examples of suitable first widths include widths between about 10 mm and about 40 mm, widths between about 18 mm and about 32 mm, and widths between about 22 mm and about 28 mm. Examples of suitable second widths include widths between about 8 mm and about 30 mm, widths between about 14 mm and about 24 mm, and widths between about 17 mm and about 21 mm. Examples of suitable fourth widths include widths between about 6 mm and about 24 mm, widths between about 10 mm and about 20 mm, and widths between about 13 mm and about 16 mm. Examples of suitable third widths include widths between about 4 mm and about 20 mm, widths between about 8 mm and about 16 mm, and widths between about 10 mm and about 14 mm.

The upper surface 420 defines protruding ridges 460 integrally formed with the main body 402 that are adapted to stabilize the intervertebral spacer 400 after implantation within a body. More specifically, the upper surface 420 has seven protruding ridges 460, including a first protruding ridge 462 and a seventh protruding ridge 464. The first and seventh protruding ridges 462, 464 respectively define first and seventh ridge tips 463, 465. The protruding ridges 460 may be integrally formed with the main body 402, as illustrated in the Figures, or can comprise one or more separate members directly or indirectly attached to the main body 402 via adhesives, welding, a mechanical connector, or another suitable attachment mechanism in other embodiments. A skilled artisan will be able to determine suitable sizes and shapes of the protruding ridges according to a particular example based on various considerations, including the position at which the intervertebral spacer will be implanted within the spinal column and the dimensions of the opening into which the intervertebral spacer will be implanted. Examples of other suitable structures that may be used in place of protruding ridges include indented surfaces, protruding ribs, and wave-like structures having a pointed apex and rounded valleys. In other embodiments, the upper surface may define more than or less than seven protruding ridges.

The first protruding ridge 462 is the protruding ridge 460 that is disposed closest to the exterior proximal wall 410. The seventh protruding ridge 464 is the protruding ridge 460 disposed closest to the exterior distal wall 412. The first ridge tip 463 is disposed on a first plane 466 that is parallel to a horizontal axis (not illustrated in the Figures). The second ridge tip 465 is disposed on a second plane 468 that forms an upper surface angle γ with respect to the first plane 466 on which the first ridge tip 463 lies. The intervertebral spacer may define any upper surface angle γ. A skilled artisan will be able to determine a suitable upper surface angle for the intervertebral spacer according to a particular example based on various considerations, including the position at which the intervertebral spacer will be implanted within the spinal column and the dimensions of the opening into which the intervertebral spacer will be implanted. Examples of suitable upper surface angles include angles between about 0° and about 10°, angles between about 2° and about 8°, and angles between about 4° and about 6°.

The lower surface 422 is generally rounded trapezoidal in shape and defines a generally rounded trapezoidal cutout 423. The lower surface 422 defines a first edge 470 at which the lower surface 422 is adjacent the exterior proximal wall 410 and each of the first and second exterior lateral walls 414, 416. The first edge 470 defines a fifth width $w_5$ extending from a first point 471 disposed on the first edge 470 to a second point 472 disposed on the first edge 470. The first and second points 471, 472 are disposed on the first edge 470 such that they are adjacent the first and second exterior lateral walls 414, 416, respectively. The lower surface 422 also defines a second edge 474 at which the lower surface 422 is adjacent the interior proximal wall 430 and each of the first and second interior lateral walls 434, 436. The second edge 474 defines a sixth width $w_6$ extending from a third point 475 disposed on the second edge 474 to a fourth point 476 disposed on the second edge 474. The third and fourth points 475, 476 are disposed on the second edge 474 such that they are adjacent the first and second interior lateral walls 434, 436, respectively. Furthermore, the lower surface 422 defines a third edge 477 at which the lower surface 422 is adjacent the interior distal wall 432 and each of the first and second interior lateral walls 434, 436. The third edge 477 defines a seventh width $w_7$ extending from a fifth point 478 disposed on the third edge 477 to a sixth point 479 disposed on the third edge 477. The fifth and sixth points 478, 479 are disposed on the third edge 477 such that they are adjacent the first and second interior lateral walls 434, 436, respectively. The lower surface 422 also defines a fourth edge 480 at which the lower surface 422 is adjacent the exterior distal wall 412 and each of the first and second exterior lateral walls 414, 416. The fourth edge 480 defines an eighth width $w_8$ extending from a seventh point 481 disposed on the fourth edge 480 to an eighth point 482 disposed on the fourth edge 480. The seventh and eighth points 481, 482 are disposed on the fourth edge 480 such that they are adjacent the first and second exterior lateral walls 414, 416, respectively.

In the illustrated embodiment, the fifth width $w_5$ is greater than the eighth width $w_8$, the eighth width $w_8$ is greater than the sixth width $w_6$, and the sixth width $w_6$ is greater than the seventh width $w_7$. However, an individual fifth, sixth, seventh, or eighth width $w_5$, $w_6$, $w_7$, $w_8$ may be greater than, equal to, about equal to, or less than any other individual fifth, sixth, seventh, or eighth width $w_5$, $w_6$, $w_7$, $w_8$. The lower surface can define any suitable fifth, sixth, seventh, and eighth width. A skilled artisan will be able to select appropriate fifth, sixth, seventh, and eighth widths according to a particular example based on various considerations, including the position at which the intervertebral spacer will be implanted within the spinal column, and the dimensions of the opening into which the intervertebral spacer will be implanted. Examples of suitable fifth widths include widths between about 8 mm and about 22 mm, widths between about 11 mm and about 19 mm, and widths between about 14 mm and about 16 mm. Examples of suitable eighth widths include widths between about 6 mm and about 20 mm, widths between about 9 mm and about 17 mm, and widths between about 12 mm and about 14 mm. Examples of suitable sixth widths include widths between about 4 mm and about 18 mm, widths between about 7 mm and about 15 mm, and widths between about 10 mm and about 12 mm. Examples of suitable seventh widths include widths between about 2 mm and about 16 mm, widths between about 5 mm and about 13 mm, and widths between about 8 mm and about 11 mm.

The lower surface 422 defines protruding ridges 469 integrally formed with the main body 402 that are adapted to stabilize the intervertebral spacer 400 after implementation. More specifically, the lower surface 422 defines seven protruding ridges 469, including a first protruding ridge 572 and a seventh protruding ridge 574. The first and seventh protruding ridges 572, 574 respectively define first and seventh ridge tips 573, 575. The protruding ridges 469 may be integrally formed with the main body 402, as illustrated in the Figures, or can comprise one or more separate members directly or indirectly attached to the main body 402 via adhesives, welding, a mechanical connector, or another suitable attachment mechanism in other embodiments. A skilled artisan will be able to determine suitable sizes and shapes of the protruding ridges based on various considerations, including the position at which the intervertebral spacer will be implanted within the spinal column and the dimensions of the opening into which the intervertebral spacer will be implanted. Examples of other suitable structures that may be used in place of protruding ridges include indented surfaces, protruding ribs, and wave-like structures having a pointed apex and rounded valleys. In other embodiments, the lower surface may define more than or less than seven protruding ridges.

The first protruding ridge 572 is the protruding ridge 469 that is disposed closest to the exterior proximal wall 410. The seventh protruding ridge 574 is the protruding ridge 469 disposed closest to the exterior distal wall 412. The first ridge tip 573 is disposed on a first plane 576 that is parallel to a horizontal axis (not illustrated in the Figures). The second ridge tip 575 is disposed on a second plane 578 that forms a lower surface angle υ with respect to the first plane 576 on which the first ridge tip 573 lies. The intervertebral spacer may define any lower surface angle υ. A skilled artisan will be able to determine a suitable lower surface angle for the intervertebral spacer according to a particular example based on various considerations, including the position at which the intervertebral spacer will be implanted within the spinal column and the dimensions of the opening into which the intervertebral spacer will be implanted. Examples of suitable upper surface angles include angles between about 0° and about 10°, angles between about 2° and about 8°, and angles between about 4° and about 6°.

The main body 402 also defines first, second, and third slots 483, 484, 485. Each of the first, second, and third slots 483, 484, 485 is cylindrical, extends from the upper surface 420 to the lower surface 422 of the main body 402, and contains an axis (not illustrated in the Figures) that is parallel to the longitudinal axis (not illustrated in the Figures). The first, second, and third slots 483, 484, 485 respectively define first, second, and third upper openings 583, 584, 585 disposed on the upper surface 420 and also respectively define first, second, and third lower openings 593, 594, 595 disposed on the lower surface 422. The first and second slots 483, 484 are disposed proximal to the interior proximal wall 430; the third slot 485 is disposed distal to the interior distal wall 432. The first, second, and third slots 483, 484, 485 may have any shape and size and may be aligned in any manner within the main body 402 relative to one another. A skilled artisan will be able to determine suitable slot shapes and positions according to a particular example based on various considerations, including the position at which the intervertebral spacer will be implanted within the spinal column and the dimensions of the opening into which the intervertebral spacer will be implanted. In other embodiments, the first, second, and third slots may be cube-shaped, conical, or frustoconical. Additionally, in other embodiments zero, one, two, four, or more than four slots may be defined by the main body. The axes defined by the slots may also be parallel to, substantially parallel to, perpendicular to, substantially perpendicular to, or disposed at an angle with respect to the longitudinal axis. Moreover, an individual slot may be sized and shaped the same as or differently than any other individual slot in other embodiments.

Figure 13:
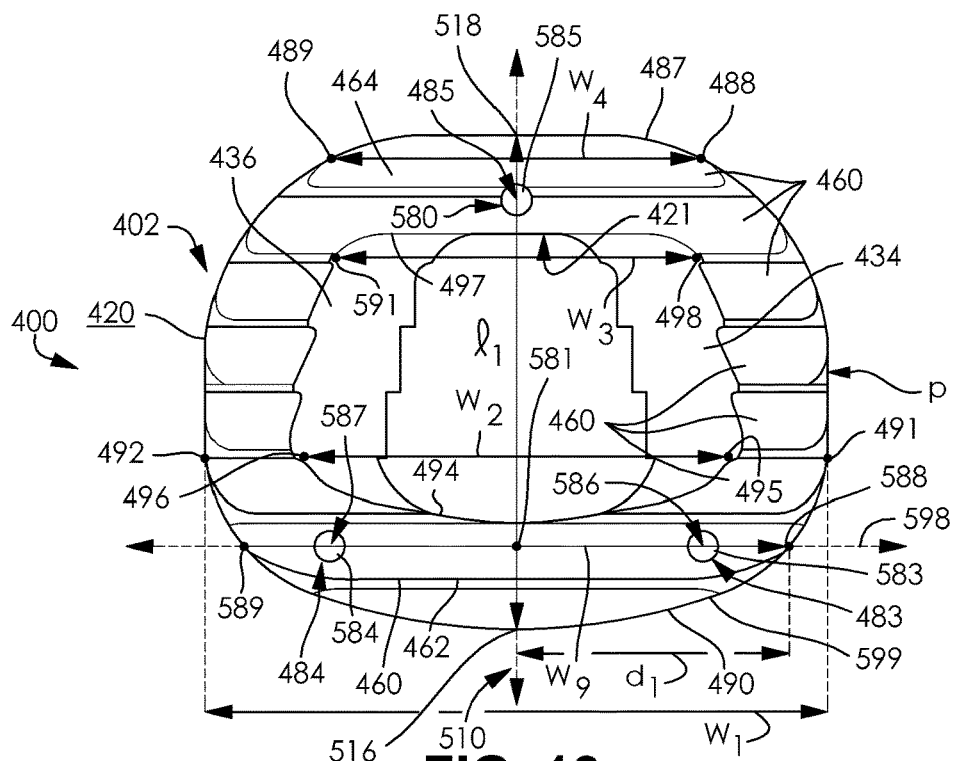
FIG. 13 is a top view of the intervertebral spacer illustrated in FIG. 11A.
Figure 14:
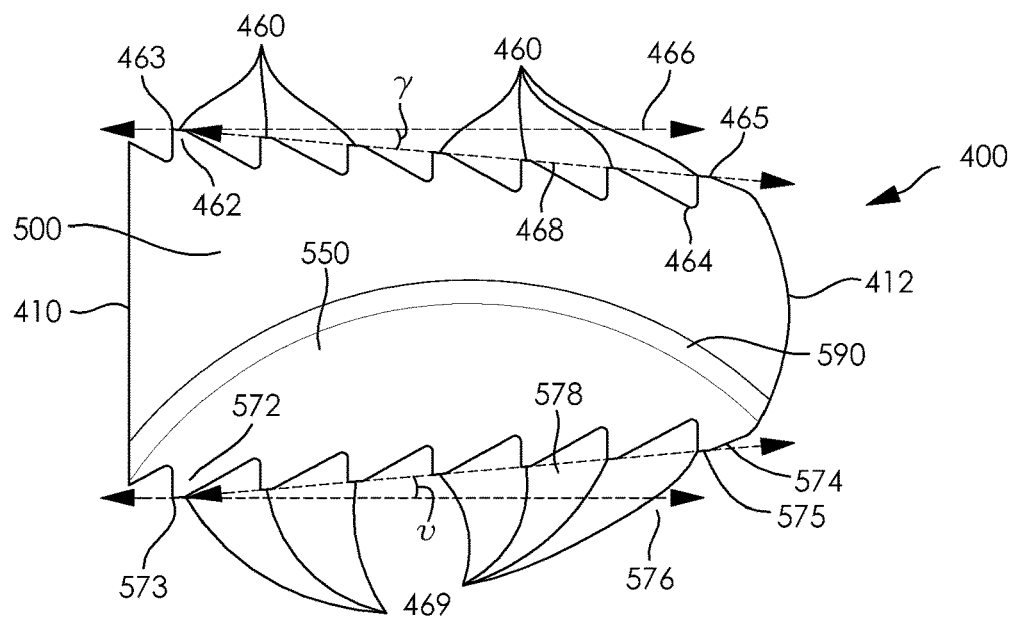
FIG. 14 is a side view of the intervertebral spacer illustrated in FIG. 11A.
Figure 15:
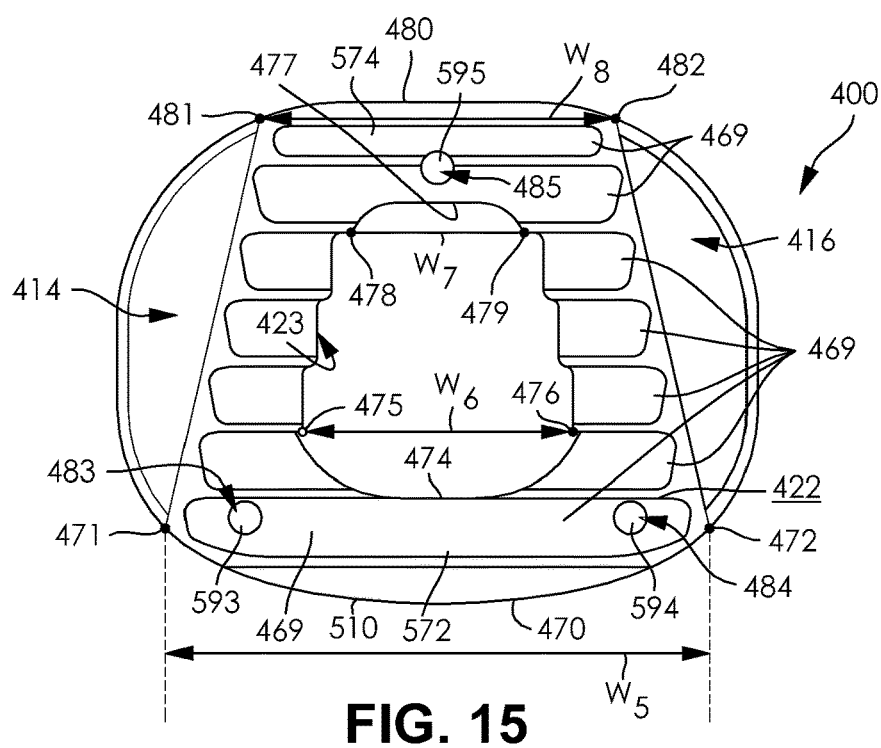
FIG. 15 is a bottom view of the intervertebral spacer illustrated in FIG. 11A.

FIG. 13 best illustrates a ninth width $w_9$. The ninth width $w_9$ is disposed on a plane 598 that extends through the respective first and second centers 586, 587 of the first and second slots 483, 484. The plane 598 also extends through a first point 588 disposed on the first edge 490, a second point 589 disposed on the first edge 490, and a midpoint 581 that is equidistant from the first and second points 588, 589. The upper surface 420 defines a first distance $d_1$ extending from the midpoint 581 to the first point 588 along the plane 598. Additionally, as described above, the continuous perimeter 599 defines a perimeter length p. The upper surface 420 can define any ninth width $w_9$, first distance $d_1$, and perimeter length p. In the illustrated embodiment, the ninth width $w_9$ is less than the first width $w_1$, but greater than the second width $w_2$. A skilled artisan will be able to determine suitable a perimeter length, ninth width, and first distance according to a particular example based on various considerations, including the position at which the intervertebral spacer will be implanted within the spinal column and the dimensions of the opening into which the intervertebral spacer will be implanted. Examples of suitable first distances include distances between about 1 mm and about 5 mm and distances between about 2 mm and about 4 mm. Examples of suitable perimeter lengths include perimeter lengths between about 6 mm and about 50 mm and perimeter lengths between about 20 mm and about 36 mm. In addition, in another embodiment, the perimeter length may be determined by a mathematical formula:

$$p = \frac{d^2 + \left(\frac{w_1}{2}\right)^2}{2d}$$

where p is the perimeter length, d is the first distance, and $w_1$ is the first width.

The upper surface 420 also defines a first length $l_1$. The first length $l_1$ is disposed on a plane 510 that extends through the center 580 of the third slot 485 from a first point 516 disposed on the continuous perimeter 599 to a second point 518 disposed on the continuous perimeter 599. The upper surface 420 may define any first length $l_1$. A skilled artisan will be able to determine a suitable first length of the upper surface according to a particular example based on various considerations, including the position at which the intervertebral spacer will be implanted within the spinal column and the dimensions of the opening into which the intervertebral spacer will be implanted. Examples of suitable first lengths include lengths between about 8 mm and about 18 mm, lengths between about 10 mm and about 16 mm, and lengths between about 12 mm and about 14 mm.

Figure 16:
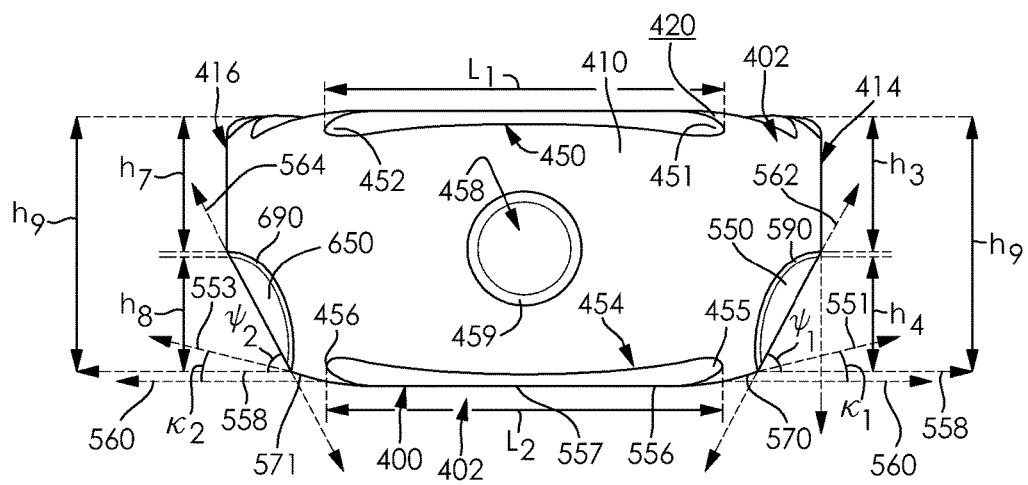
FIG. 16 is an end view of the intervertebral spacer illustrated in FIG. 11A.

FIG. 16 best illustrates the exterior proximal wall 410. The exterior proximal wall 410 and lower surface 422 cooperatively define first and second grooves 450, 454. The first groove 450 is defines a first groove length $L_1$ extending from a first groove end 451 to a second groove end 452; the second groove 454 defines a second groove length $L_2$ extending from a third groove end 455 to a fourth groove end 456. The second groove 454 also includes an upper portion 555 extending from the third groove end 455 to the fourth groove end 456 and a lower portion 556 extending from the third groove end 455 to the fourth groove end 456. The lower portion 556 has a center point 557 disposed on a lower portion plane 558; the center point 557 is disposed at the midpoint of the lower portion 556, between the third and fourth groove ends 455, 456. Each of the first and second grooves 450, 452 is elongate and semi-elliptical in shape and is integrally formed with the main body 402. In this embodiment, the first groove length $L_1$ is equal to the second groove length $L_2$. The first and second grooves 450, 454 may have any shapes and sizes, however. A skilled artisan will be able to determine whether to include grooves and how best to size, shape, and align them according to a particular example based on various considerations, including the position at which the intervertebral spacer will be implanted within the spinal column and the dimensions of the opening into which the intervertebral spacer will be implanted. In other examples, the first groove length may be greater than, about equal to, or less than the second groove length. Additionally, in alternative examples the exterior proximal wall may define zero, one, three, four, or more than four grooves and each groove may have any shape and define any length.

FIG. 16 also illustrates first and second connecting portions 570, 571 cooperatively defined by the proximal wall 410, the second groove 454, the lower surface 422, and one of the first and second exterior lateral walls 414, 416, respectively. The first connecting portion 570 extends from where the lower portion 556 is adjacent the third groove end 455 and the lower surface 422 to the chamfered portion 590 (described below) of the first exterior lateral wall 414. The second connecting portion 571 extends from where the lower portion 556 is adjacent the fourth groove end 456 and the lower surface 422 to the chamfered portion 690 (described below) of the second exterior lateral wall 416. The first connecting portion 570 is disposed on a first connecting plane 551 and the second connecting portion 571 is disposed on a second connecting plane 553. The first connecting plane 551 forms a first connecting angle $\kappa_1$ with respect to the lower portion plane 558 and the second connecting plane 553 forms a second connecting angle $\kappa_2$ with respect to the lower portion plane 558. A skilled artisan will be able to determine suitable first and second connecting angles for the intervertebral spacer according to a particular example based on various considerations, including the position at which the intervertebral spacer will be implanted within the spinal column and the dimensions of the opening into which the intervertebral spacer will be implanted. Examples of suitable first connecting angles include angles between about 90° and about 150°, angles between about 110° and about 140°, and angles between about 120° and about 130°. Examples of suitable second connecting angles include angles between about −90° and about −150°, angles between about −110° and about −140°, and angles between about −120° and about −130°. While the first connecting angle $\kappa_1$ is equal to the second connecting angle $\kappa_2$ in the illustrated embodiment, in other embodiments the first connecting angle may be greater than, about equal to, or less than the second connecting angle. Additionally, in other embodiments, the first and second connecting portions may be disposed on the same plane as the lower surface or any of the protruding ridges defined by the lower surface and may, thus, have different angular measurements relative to the lower portion plane. The first and second connecting portions also may each comprise a bell curve, an S-curve, a parabolic curve, or any other suitable type of curve, rather than an angled portion, in alternative embodiments.

Figure 16A:
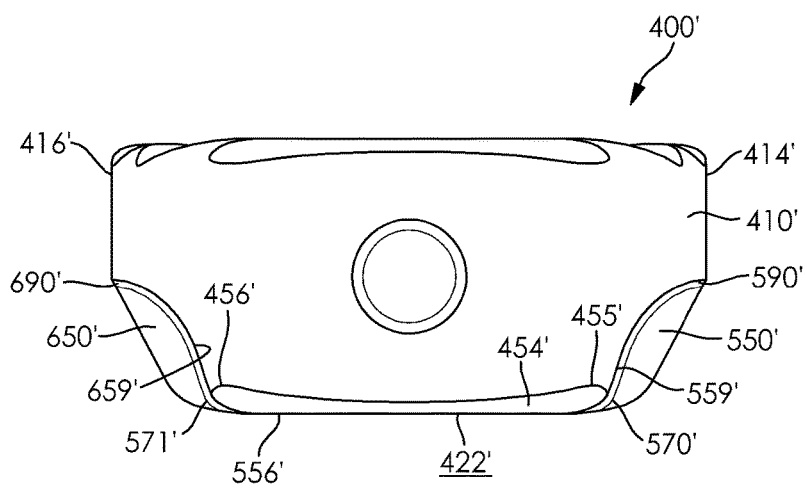
FIG. 16A is an end view of an alternative intervertebral spacer.

The first and second connecting portions may, however, comprise any suitable shape or structure in other alternatives. FIG. 16A illustrates an alternative intervertebral spacer 400'. In the illustrated alternative intervertebral spacer 400', the first connecting portion 570' is cooperatively defined by the exterior proximal wall 410' and the first exterior lateral wall 414' and extends from where the lower portion 556' of the second groove 454' is adjacent the third groove end 455' and the lower surface 422' to the chamfered portion 590'. The second connecting portion 571' is cooperatively defined by the exterior proximal wall 410' and the second exterior lateral wall 416' and extends from where the lower portion 556' is adjacent the fourth groove end 456' and the lower surface 422' to the chamfered portion 690'. Rather than being angled in a manner similar to the first and second connecting portions 570, 571, the first and second connecting portions 570', 571' of intervertebral spacer 400' are curved. More specifically, the first connecting portion 570' defines a first S-curve 559' adjacent the chamfered portion 590' of the first exterior lateral wall 414'. Similarly, the second connecting portion 571' defines a second S-curve 659' adjacent the chamfered portion 690' of the second exterior lateral wall 416'. The second S-curve 659' is a mirror image of the first S-curve 559'. A skilled artisan will be able to determine suitable shapes for the first and second connecting portions according to a particular example based on various considerations, including the position at which the intervertebral spacer will be implanted within the spinal column and the dimensions of the opening into which the intervertebral spacer will be implanted. The first and second connecting portions may each comprise a bell curve, an S-curve that is elongated or shortened in relation to the illustrated first and second S-curves, a parabolic curve, or any other suitable type of curve in other alternatives. In addition, the first and second connecting portions may be angled, rather than curved, and may have any suitable angular measurement in other alternatives.

Additionally, in this embodiment each of the second portion 550' of the first exterior lateral wall 414' and the second portion 650' of the second exterior lateral wall 416' are non-uniformly grooved. That is, each of the second portions 550', 650' extends further inwardly, toward the interior cavity (not illustrated in the Figure), where the second portions 550', 650' are adjacent the exterior proximal wall 410' than where they are adjacent the exterior distal wall (not illustrated in the Figure). In the illustrated embodiment, the second portion 650' is substantially a mirror image of the second portion 550'. A skilled artisan will be able to select how best to configure each of the second portions based on various considerations, including the position at which the intervertebral spacer will be implanted within the spinal column and the dimensions of the opening into which the intervertebral spacer will be implanted. In a different alternative, the second portions may comprise a scoop, a void, or a depression and may or may not be mirror images of one another. In such an alternative, one of the second portions may extend further towards the interior cavity adjacent the exterior proximal wall or exterior distal wall than the other second portion. In another alternative, one or both of the second portions may be grooved such that they extend further inward, toward the interior cavity, where the one or more second portions are adjacent the exterior distal wall than where they are adjacent the exterior proximal wall. Other alternatives exist in which only one of the second portions comprises a groove or each of the second portions comprises a uniform groove.

Figure 16B:
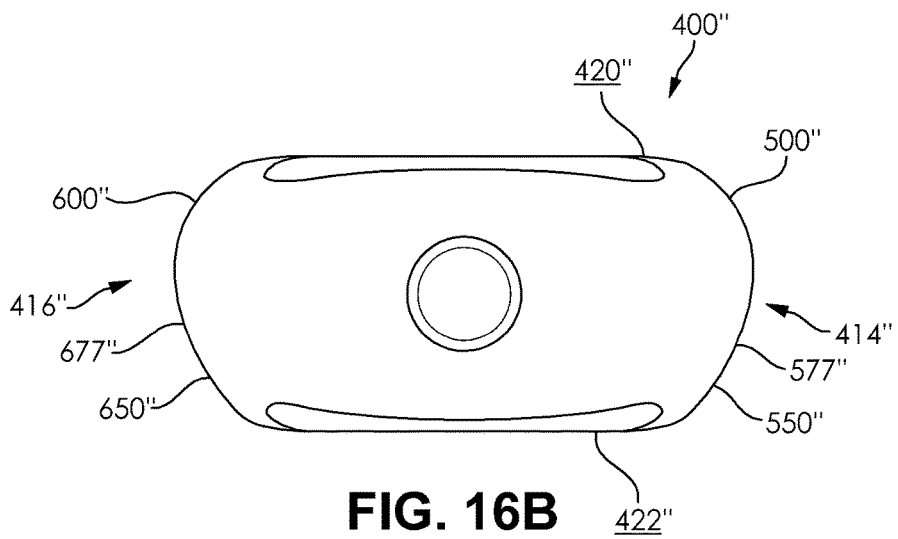
FIG. 16B is an end view of another alternative intervertebral spacer.

FIG. 16B illustrates another alternative intervertebral spacer 400". The first portion 500" of the intervertebral spacer 400" is adjacent the second portion 550" of the first exterior lateral wall 414"; it does not include a chamfered portion defined by the first exterior lateral wall 414". The first and second portions 500", 550" cooperatively define a first curve 577" extending from the lower surface 422" to the upper surface 420" of the intervertebral spacer 400" and make up the first exterior lateral wall 414". The first portion 500" is outwardly-directed relative to the longitudinal axis (not illustrated in the Figures). The second portion 550" is also outwardly-directed relative to the longitudinal axis. A skilled artisan will be able to determine how best to configure and angle the first and second portions relative to the longitudinal axis in a particular embodiment based on various considerations, including the position at which the intervertebral spacer will be implanted within the spinal column and the dimensions of the opening into which the intervertebral spacer will be implanted. In some embodiments, only the first portion may be outwardly-directed relative to the longitudinal axis. In other embodiments, only the second portion may be outwardly-directed relative to the longitudinal axis. Additionally, the first portion may be outwardly-directed to a different degree than the second portion relative to the longitudinal axis.

The first portion 600" is adjacent the second portion 650" of the second exterior lateral wall 416" in this embodiment; it also does not include a chamfered portion defined by the second exterior lateral wall 416". The first and second portions 600", 650" cooperatively define a second curve 677" extending from the lower surface 422" to the upper surface 420" of the intervertebral spacer 400" and make up the second exterior lateral wall 416". The first portion 600" is outwardly-directed relative to the longitudinal axis (not illustrated in the Figures). The second portion 650" is also outwardly-directed relative to the longitudinal axis. A skilled artisan will be able to determine how best to configure and angle the first and second portions relative to the longitudinal axis in a particular embodiment based on various considerations, including the position at which the intervertebral spacer will be implanted within the spinal column and the dimensions of the opening into which the intervertebral spacer will be implanted. In some embodiments, only the first portion may be outwardly-directed relative to the longitudinal axis. In other embodiments, only the second portion may be outwardly-directed relative to the longitudinal axis. Additionally, the first portion may be outwardly-directed to a different degree than the second portion relative to the longitudinal axis.

Note that one or both of the alternative structures shown in FIG. 16B can be included in an intervertebral spacer according to a particular embodiment. Accordingly, in a particular embodiment, each of the first portion of the first exterior lateral wall and the first portion of the second exterior lateral wall may be outwardly-directed relative to the longitudinal axis, while the second portion of the first exterior lateral wall and the second portion of the second exterior lateral wall may be inwardly-directed relative to the longitudinal axis or may comprise a planar surface. In another particular embodiment, each of the second portion of the first exterior lateral wall and the second portion of the second exterior lateral wall may be outwardly-directed relative to the longitudinal axis, while the first portion of the first exterior lateral wall and the first portion of the second exterior lateral wall may be inwardly-directed relative to the longitudinal axis or may comprise a planar surface.

As illustrated in FIG. 16, the exterior proximal wall 410 defines a passageway 458 extending directly from the exterior proximal wall 410 to the interior proximal wall 430. The passageway 458 defines a circular opening 459 on the exterior proximal wall 410 and is configured for the insertion of a device used in the placement of the intervertebral spacer 400. The passageway 458 can have any suitable shape. A skilled artisan will be able to select an appropriate shape for the passageway according to a particular example based on various considerations, including the position at which the intervertebral spacer will be implanted within the spinal column and the dimensions of the opening into which the intervertebral spacer will be implanted. Examples of suitable passageway shapes include square, triangular, rectangular, and elliptical.

The first exterior lateral wall 414 is chamfered in the illustrated embodiment and includes a first portion 500, a second portion 550, and a chamfered portion 590 disposed between the first portion 500 and the second portion 550. Any portion of the first exterior lateral wall 414 may be chamfered, however. A skilled artisan will be able to determine how to suitably chamfer a portion of the first exterior lateral wall according to a particular example based on various considerations including the position at which the intervertebral spacer will be implanted within the spinal column and the dimensions of the opening into which the intervertebral spacer will be implanted. In other embodiments, the first exterior lateral wall may include a beveled, rounded, angled, curved or filleted portion.

The first portion 500 of the first exterior lateral wall 414 defines a first height $h_1$ at its most proximal portion 501 that extends from a first point 502 disposed adjacent the upper surface 420 to a second point 504 disposed adjacent the lower surface 422. The first exterior lateral wall 414 defines a second height $h_2$ distal to the first height $h_1$ that extends from a third point 512 disposed adjacent the upper surface 420 to a fourth point 514 disposed adjacent the lower surface 422. In addition, the first portion 500 defines a third height $h_3$ that is defined by fifth and sixth points 522, 524. The fifth point 522 is adjacent the upper surface 420 and the sixth point 524 is adjacent the chamfered portion 590. The plane (not illustrated in the Figures) on which the fifth and sixth points 522, 524 lie is equidistant from the exterior proximal wall 410 and the exterior distal wall 412. In the illustrated embodiment, the first height $h_1$ is greater than the second height $h_2$ and the first and second heights $h_1$, $h_2$ are each greater than the third height $h_3$. Thus, the first exterior lateral wall 414 defines a first portion 500 that first tapers in the distal direction, then widens in the distal direction. The first exterior lateral wall can have any suitable first, second, and third heights $h_1$, $h_2$, $h_3$, however. A skilled artisan will be able to select appropriate first, second, and third heights according to a particular example based on various considerations, including the position at which the intervertebral spacer will be implanted within the spinal column and the dimensions of the opening into which the intervertebral spacer will be implanted. In other embodiments, the first height may be greater than, less than, or about equal to the second height. In other alternatives, the first exterior lateral wall or a portion thereof may continuously taper in the distal direction, continuously widen in the distal direction, or stay uniform in height along the first exterior lateral wall. The third height may also be greater than, less than, or equal to one third of the height of the first and second heights in various embodiments.

The second portion 550 of the first exterior lateral wall 414 is a groove that has a substantially arcuate perimeter and is adjacent the chamfered portion 590. The second portion 550 defines a fourth height $h_4$ extending from a seventh point 552 adjacent the chamfered portion 590 to an eighth point 554 adjacent the lower surface 422. In the illustrated embodiment, the fourth height $h_4$ is approximately two times greater than the third height $h_3$. The second portion 550 can have any suitable fourth height $h_4$, however. A skilled artisan will be able to determine a suitable fourth height according to a particular example based on various considerations, including the position at which the intervertebral spacer will be implanted within the spinal column and the dimensions of the opening into which the intervertebral spacer will be implanted. In other embodiments the fourth height may be less than, greater than, equal to, or about equal to the third height. Additionally, the second portion may also be elliptical, arcuate, rectangular, or circular in shape or may comprise a scoop, a void, or a depression.

The second exterior lateral wall 416 is substantially a mirror image of the first exterior lateral wall 414 in the illustrated example intervertebral spacer 400; thus, each of the first and second exterior lateral walls 414, 416 has substantially the same structure. The second exterior lateral wall may have a different structure than the first exterior lateral wall in alternative embodiments. A skilled artisan will be able to determine whether the second exterior lateral wall should be a mirror image of the first exterior lateral wall according to a particular example based on various considerations, including the position at which the intervertebral spacer will be implanted within the spinal column and the dimensions of the opening into which the intervertebral spacer will be implanted. In other embodiments, the second exterior lateral wall may not be a mirror image of the first exterior lateral wall.

Thus, the second exterior lateral wall 416 is chamfered in the illustrated embodiment and includes a first portion 600, a second portion 650, and a chamfered portion 690 disposed between the first portion 600 and the second portion 650. Any portion of the second exterior lateral wall 416 may be chamfered, however. A skilled artisan will be able to determine how to suitably chamfer a portion of the second exterior lateral wall according to a particular example based on various considerations including the position at which the intervertebral spacer will be implanted within the spinal column and the dimensions of the opening into which the intervertebral spacer will be implanted. In other embodiments, the second exterior lateral wall may include a beveled, rounded, angled, curved or filleted portion.

The first portion 600 of the second exterior lateral wall 416 defines a fifth height $h_5$ at its most proximal portion 601 that extends from a first point 602 disposed adjacent the upper surface 420 to a second point 604 disposed adjacent the lower surface 422. The second exterior lateral wall 416 defines a sixth height $h_6$ distal to the fifth height $h_5$ that extends from a third point 612 disposed adjacent the upper surface 420 to a fourth point 614 disposed adjacent the lower surface 422. In addition, the first portion 600 defines a seventh height $h_7$ that is defined by fifth and sixth points 622, 624. The fifth point 622 is adjacent the upper surface 420 and the sixth point 624 is adjacent the chamfered portion 690. The plane (not illustrated in the Figures) on which the fifth and sixth points 622, 624 lie is equidistant from the exterior proximal wall 410 and the exterior distal wall 412. In the illustrated embodiment, the fifth height $h_5$ is greater than the sixth height $h_6$ and the fifth and sixth heights $h_5$, $h_6$ are each greater than the seventh height $h_7$. Thus, the second exterior lateral wall 416 defines a first portion 600 that first tapers in the distal direction, then widens in the distal direction. The second exterior lateral wall can have any suitable fifth, sixth, and seventh heights $h_5$, $h_6$, $h_7$. A skilled artisan will be able to select appropriate fifth, sixth, and seventh heights according to a particular example based on various considerations, including the position at which the intervertebral spacer will be implanted within the spinal column and the dimensions of the opening into which the intervertebral spacer will be implanted. In other embodiments, the fifth height may be greater than, less than, or about equal to the sixth height. In other alternatives, the second exterior lateral wall or a portion thereof may continuously taper in the distal direction, continuously widen in the distal direction, or stay uniform in height along the second exterior lateral wall. The seventh height may also be greater than, less than, or equal to one third of the height of the fifth and sixth heights in various embodiments.

The second portion 650 of the second exterior lateral wall 416 is a groove that has a substantially arcuate perimeter and is adjacent the chamfered portion 690, which is curved and disposed between the first and second portions 600, 650 along the first exterior lateral wall 416. The second portion 650 defines an eighth height $h_8$ extending from a seventh point 652 adjacent the chamfered portion 690 to an eighth point 654 adjacent the lower surface 422. In the illustrated embodiment, the eighth height $h_8$ is approximately two times greater than the seventh height $h_7$. The second portion 650 can have any suitable eighth height $h_8$, however. A skilled artisan will be able to determine a suitable eighth height according to a particular example based on various considerations, including the position at which the intervertebral spacer will be implanted within the spinal column and the dimensions of the opening into which the intervertebral spacer will be implanted. In other embodiments the eighth height may be less than, greater than, equal to, or about equal to the seventh height. Additionally, the second portion may also be elliptical, arcuate, rectangular, or circular in shape or may comprise a scoop, a void, or a depression. Furthermore, in any embodiment, either or both of the second portions of the first exterior lateral wall and the second exterior lateral wall may not include a groove, scoop, void, or depression.

As described above, the first and second exterior lateral walls 414, 416 may include chamfered, beveled, rounded, or filleted portions in various embodiments, each of which accommodates implantation of the intervertebral spacer 400 between any two vertebrae. Intervertebral spacer 400 includes first and second exterior lateral walls 414, 416 that are partially chamfered and define grooves, in the form of the second portions 550, 650, in order to accommodate the curvature of the uncovertebral joint (described below). The inventors have determined that the intervertebral spacer 400 is particularly suitable for implantation between the first cervical vertebra and the second cervical vertebra, the second cervical vertebra and the third cervical vertebra, the third cervical vertebra and the fourth cervical vertebra, the fourth cervical vertebra and the fifth cervical vertebra, the fifth cervical vertebra and the sixth cervical vertebra, the sixth cervical vertebra and the seventh cervical vertebra, or the seventh cervical vertebra and the first thoracic vertebra. The intervertebral spacer 400, however, may be implanted between any two vertebrae.

FIG. 16 best illustrates the angular dimensions of the second portions 550, 650. The lower surface 422 lies on a first outer plane 560 that is perpendicular to a horizontal axis (not illustrated in the Figures). In addition, each of the sixth point 524 disposed on the first exterior lateral wall 414 and the eighth point 554 disposed on the second portion 550 of the first exterior lateral wall 414 lie on a second outer plane 562. Each of the sixth point 624 disposed on the second exterior lateral wall 416 and the eighth point 654 disposed on the second portion 650 of the second exterior lateral wall 416 lie on a third outer plane 564. The second and third outer planes 562, 564 form first and second exterior angles $\psi_1$, $\psi_2$, respectively, with respect to the first outer plane 560. The first and second exterior angles $\psi_1$, $\psi_2$ can have any suitable angular measurement. A skilled artisan will be able to determine suitable first and second exterior angles according to a particular example based on various considerations, including the position at which the intervertebral spacer will be implanted within the spinal column and the dimensions of the opening into which the intervertebral spacer will be implanted. Examples of suitable first exterior angles include angles between about 30° and about 75°, angles between about 42° and about 63°, and angles between about 50° and about 55°. Examples of suitable second exterior angles include angles between about −30° and about −75°, angles between about −42° and about −63°, and angles between about −50° and about −55°.

The exterior proximal wall 410 defines a ninth height $h_9$ extending from the first ridge tip 573 of the lower surface 422 to the first ridge tip 463 of the upper surface 420. The ninth height $h_9$ is greater than each of the third and seventh heights $h_3$, $h_9$ in this embodiment. The exterior proximal wall 410 can define any suitable ninth height $h_9$. A skilled artisan will be able to determine an appropriate ninth height for the exterior proximal wall according to a particular example based on various considerations, including the position at which the intervertebral spacer will be implanted within the spinal column and the dimensions of the opening into which the intervertebral spacer will be implanted. In an alternative embodiment, the ninth height may be less than each of the third and seventh heights. In a different embodiment, the ninth height may be about equal to the third and seventh heights. The ninth height may be greater than the third and seventh heights by any amount as well. In an alternative embodiment, the ninth height may be determined by a mathematical formula:

$$h_9 = h_3 + \frac{w_1 - w_2}{2} \tan \psi_1$$

where $h_9$ is the ninth height, $h_3$ is the third height, $w_1$ is the first width, $w_2$ is the second width, $\psi_1$ is the first exterior angle $\psi_1$, the third height $h_3$ is greater than zero, and the first width $w_1$ is greater than the second width $w_2$.

Figure 17:
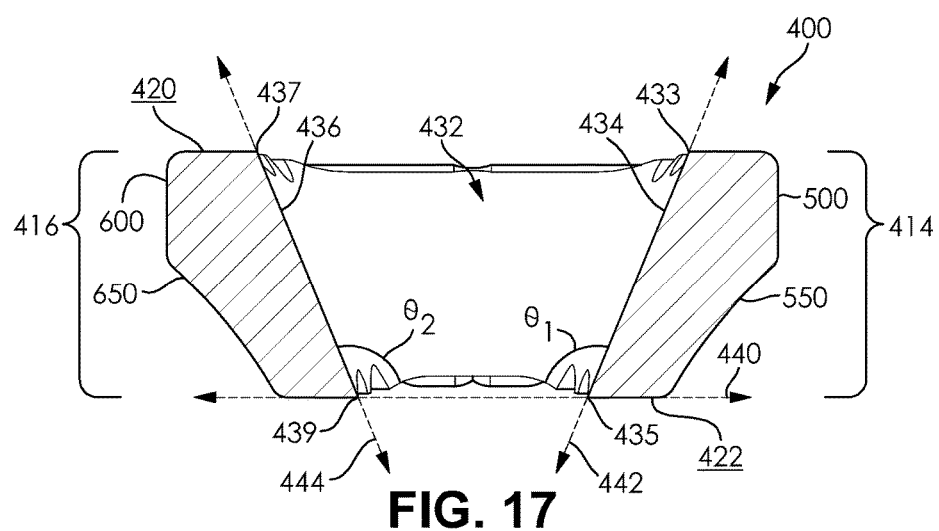
FIG. 17 is a cross-sectional view of the intervertebral spacer illustrated in FIG. 11A taken along line 17-17.

In this embodiment, as best illustrated in FIG. 17, the first interior lateral wall 434 extends from a first point 433 disposed adjacent the upper surface 420 to a second point 435 disposed adjacent the lower surface 422. The second point 435 is disposed on a first plane 440 that is perpendicular to a horizontal axis (not illustrated in the Figures). The first interior lateral wall 434 is disposed on a second plane 442 that forms a first interior outward angle $\theta_1$ relative to the first plane 440. Additionally, the second interior lateral wall 436 extends from a third point 437 disposed adjacent the upper surface 420 to a fourth point 439 disposed adjacent the lower surface 422. The fourth point 439 is disposed on the first plane 440. The second interior lateral wall 436 is disposed on a third plane 444 that forms a second interior outward angle $\theta_2$ relative to the first plane 440. The first and second interior lateral walls 434, 436 can define any first and second interior outward angles $\theta_1$, $\theta_2$. A skilled artisan will be able to determine appropriate first and second interior outward angles for the first and second interior lateral walls according to a particular embodiment based on various considerations, including the position at which the intervertebral spacer will be implanted within the spinal column and the dimensions of the opening into which the intervertebral spacer will be implanted. Examples of suitable first interior outward angles include angles between about 90° and about 125°, angles between about 98° and about 117°, and angles between about 104° and about 111°. Examples of suitable second interior outward angles include angles between about −90° and about −125°, angles between about −98° and about −117°, and angles between about −104° and about −111°.

The second portion of the first exterior lateral wall and the second portion of the second exterior lateral wall may each be configured in particular embodiments to accommodate various uncovertebral anatomies. For example, each of the second portion of the first exterior lateral wall and the second portion of the second exterior lateral wall may be inwardly-directed relative to the longitudinal axis (as is illustrated, for example, in the embodiments illustrated in FIGS. 16 and 16A, respectively), be outwardly-directed relative to the longitudinal axis (as is illustrated, for example, in FIG. 16B), or even comprise a planar surface. A skilled artisan will be able to determine a suitable configuration for each of the second portions according to a particular example based on various considerations, including the actual configuration of an uncovertebral of a patient. An individual second portion may or may not be shaped the same as the other second portion.

Figure 18:
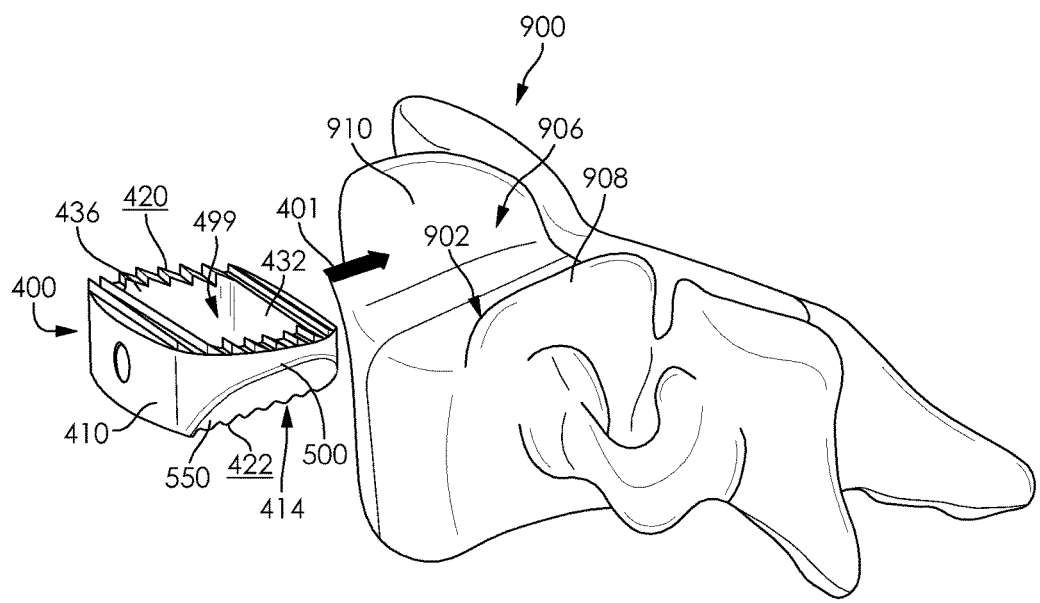
FIG. 18 is a perspective view of a vertebra from a human vertebral column and the intervertebral spacer illustrated in FIG. 11A.

As illustrated in FIG. 18, the human vertebra 900 includes an uncovertebral joint 902 and an uncovertebral space 906.

In this example, an intervertebral spacer such as intervertebral spacer 400 is inserted, as indicated by Arrow 401, above the uncovertebral joint 902. The first and second exterior lateral walls 414, 416 include grooves as described above in order to accommodate implantation of the intervertebral spacer 400 in contact with the uncovertebral joint 902. The first and second exterior lateral walls 414, 416 are adapted to contact the curved first and second walls 908, 910, respectively, of the uncovertebral joint 902. This allows the intervertebral spacer 400 to fit into the intervertebral space between the human vertebra 900 and a second human vertebra (not illustrated in the Figures); the absence of grooved first and second exterior lateral walls 414, 416 may prevent the intervertebral spacer 400 from being able to fit into the intervertebral space between the human vertebra 900 and a second human vertebra. The inventors have determined that an intervertebral spacer having the structure described above is particularly useful in situations in which it is desirable to implant an intervertebral spacer between any two cervical vertebrae or between a first cervical vertebra and a second, non-cervical, vertebra. The intervertebral spacer 400 may be implanted between any two vertebrae, however.

Figure 19:
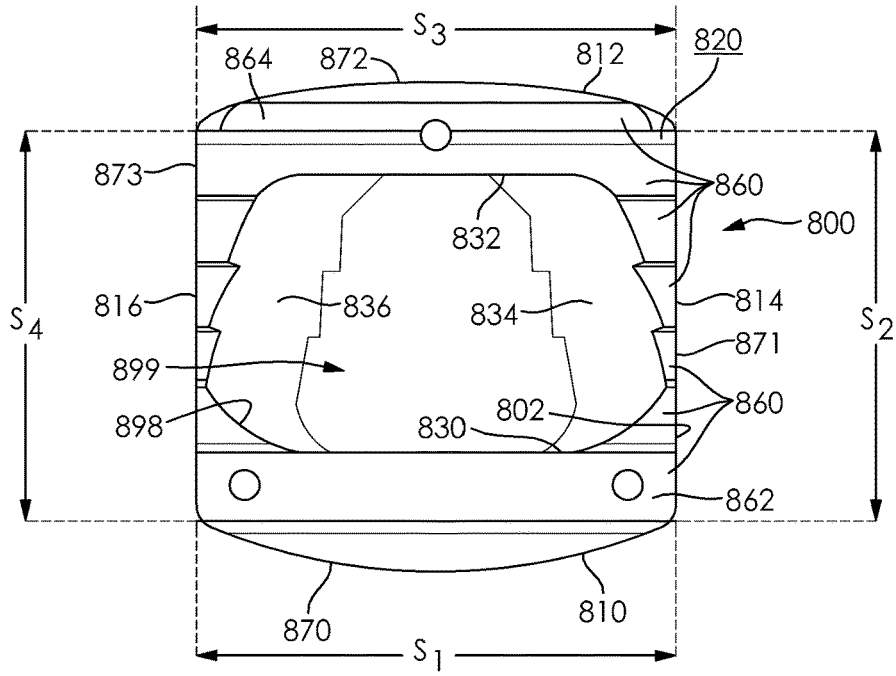
FIG. 19 is a top view of another example intervertebral spacer.
Figure 20:
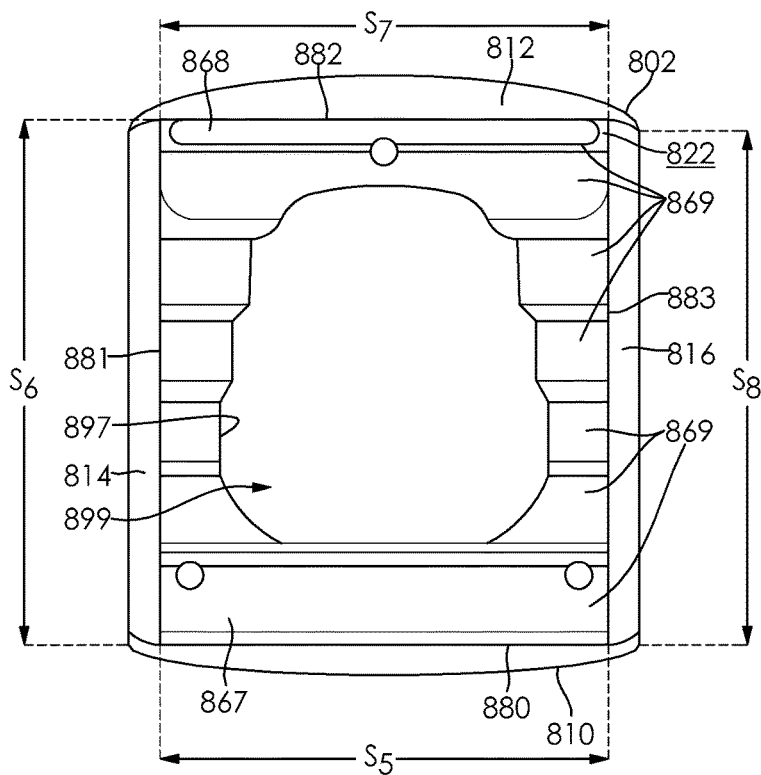
FIG. 20 is a bottom view of the intervertebral spacer illustrated in FIG. 19.

FIGS. 19 and 20 illustrate another example intervertebral spacer 800. This intervertebral spacer 800 is similar to the intervertebral spacer 400 illustrated in FIGS. 11A, 11B, 12A, 12B, 13, 14, 15, 16, 17, and 18, except as detailed below. Thus, the intervertebral spacer 800 comprises a main body 802 that defines an exterior proximal wall 810, an exterior distal wall 812, a first exterior lateral wall 814, a second exterior lateral wall 816, an interior proximal wall 830, an interior distal wall 832, a first interior lateral wall 834, a second interior lateral wall 836, an upper surface 820, a lower surface 822, and an interior cavity 899.

As best illustrated in FIG. 19, the upper surface 820 defines a generally rounded trapezoidal cutout 898 and includes four sides 870, 871, 872, 873 that form the perimeter of the upper surface 820. The first side 870 is adjacent the exterior proximal wall 810, the second side 871 is adjacent the first exterior lateral wall 814, the third side 872 is adjacent the exterior distal wall 812 and is substantially opposite the first side 870, and the fourth side 873 is adjacent the second exterior lateral wall 816 and is substantially opposite the second side 871. In the illustrated embodiment, the second and fourth sides 871, 873 each extend from the first side 870 to the third side 872, and the first and third sides 870, 872 each extend from the second side 871 to the fourth side 873. Each of the first and third sides 870, 872 is curved, while each of the second and fourth sides 871, 873 is substantially straight. Furthermore, the second side 871 is substantially parallel to the fourth side 873. The first side 870 has a length $s_1$ that is substantially equal to the length $s_3$ of the third side 872, and the second side 871 has a length $s_2$ that is substantially equal to the length $s_4$ of the fourth side 873. The upper surface 820, however, may have other shapes. A skilled artisan will be able to determine a suitable shape for the upper surface according to a particular example based on various considerations, including the position at which the intervertebral spacer will be implanted within the spinal column and the dimensions of the opening into which the intervertebral spacer will be implanted. Example suitable upper surface shapes include square, rounded rectangular, trapezoidal, circular, elliptical, and triangular. In addition, in other embodiments the first side may have a length that is greater than, about equal to, equal to, or less than the length of any of the second, third, or fourth sides. Moreover, the second side may have a length that is greater than, about equal to, equal to, or less than the length of any of the first, third, or fourth sides in alternative embodiments.

In the illustrated embodiment, the upper surface 820 defines protruding ridges 860 integrally formed with the main body 802 that are adapted to stabilize the intervertebral spacer 800 after implantation within a body. The upper surface 820 has seven protruding ridges 860, including a first protruding ridge 862 and a seventh protruding ridge 864. The protruding ridges 860 are separate members that are integrally formed with the main body 802. A skilled artisan will be able to determine suitable sizes and shapes of the protruding ridges and a suitable technique for disposing the protruding ridges on the main body according to a particular example based on various considerations, including the position at which the intervertebral spacer will be implanted within the spinal column and the dimensions of the opening into which the intervertebral spacer will be implanted. Examples of other suitable structures that may be used in place of protruding ridges include indented surfaces, protruding ribs, and wave-like structures having a pointed apex and rounded valleys. In other embodiments, the upper surface may define more than or less than seven protruding ridges. In alternative embodiments, the protruding ridges can comprise one or more separate members directly or indirectly attached to the upper surface via adhesives, welding, a mechanical connector, or another suitable attachment mechanism.

As best illustrated in FIG. 20, the lower surface 822 is generally rectangular, defines a generally rounded trapezoidal cutout 897, and includes four sides 880, 881, 882, 883 that form the perimeter of the lower surface 822. The first side 880 is adjacent the exterior proximal wall 810, the second side 881 is adjacent the first exterior lateral wall 814, the third side 882 is adjacent the exterior distal wall 812 and is substantially opposite the first side 880, and the fourth side 883 is adjacent the second exterior lateral wall 816 and is substantially opposite the second side 881. In the illustrated embodiment, the second and fourth sides 881, 883 each extend from the first side 880 to the third side 882, and the first and third sides 880, 882 each extend from the second side 881 to the fourth side 883. Each of the first, second, third, and fourth sides 880, 881, 882, 883 is substantially straight. Furthermore, the second side 881 is substantially parallel to the fourth side 883 and the first side 880 is substantially parallel to the third side 882. The first side 880 has a length $s_5$ that is substantially equal to the length $s_7$ of the third side 882, and the second side 881 has a length $s_6$ that is substantially equal to the length $s_8$ of the fourth side 883. The lower surface 822, however, may have other shapes. A skilled artisan will be able to determine a suitable shape for the lower surface according to a particular example based on various considerations, including the position at which the intervertebral spacer will be implanted within the spinal column and the dimensions of the opening into which the intervertebral spacer will be implanted. Example suitable lower surface shapes include square, rounded rectangular, trapezoidal, circular, elliptical, and triangular. In addition, in other embodiments the first side may have a length that is greater than, about equal to, equal to, or less than the length of any of the second, third, or fourth sides. Moreover, the second side may have a length that is greater than, about equal to, equal to, or less than the length of any of the first, third, or fourth sides in alternative embodiments.

In the illustrated embodiment, the lower surface 822 defines protruding ridges 869 integrally formed with the main body 802 that are adapted to stabilize the intervertebral spacer 800 after implantation within a body. The lower surface 822 has seven protruding ridges 869, including a first protruding ridge 867 and a seventh protruding ridge 868. The protruding ridges 869 are separate members that are integrally formed with the main body 802. A skilled artisan will be able to determine suitable sizes and shapes of the protruding ridges and a suitable technique for disposing the protruding ridges on the main body according to a particular example based on various considerations, including the position at which the intervertebral spacer will be implanted within the spinal column and the dimensions of the opening into which the intervertebral spacer will be implanted. Examples of other suitable structures that may be used in place of protruding ridges include indented surfaces, protruding ribs, and wave-like structures having a pointed apex and rounded valleys. In other embodiments, the lower surface may define more than or less than seven protruding ridges. In alternative embodiments, the protruding ridges can comprise one or more separate members directly or indirectly attached to the lower surface via adhesives, welding, a mechanical connector, or another suitable attachment mechanism.

In all examples, an intervertebral spacer may be formed of any suitable material, including presently known and later-developed materials for use in spinal implantation devices. A skilled artisan will be able to select an appropriate material or materials for an intervertebral spacer based on various considerations, including, but not limited to, the reason the intervertebral spacer is to be implanted within the spinal column, the size and shape of the neck and spine of a patient, the level of discomfort of the patient, the lifestyle of the patient, and the position within the spinal column at which the intervertebral spacer is to be implanted. Examples of suitable materials include, but are not limited to, polyetheretherketone ("PEEK"), stainless steel, nickel-cobalt-chromium alloys, polymeric materials, and any of a number of biocompatible materials.

The foregoing detailed description refers to example medical devices suitable for use as intervertebral spacers and includes the best mode for practicing the invention. The description and the appended drawings illustrating the described devices are intended only to provide examples and not to limit the scope of the claims in any manner.

What is claimed is:

1. An intervertebral spacer, comprising:
    a main body comprising an exterior proximal wall, an exterior distal wall, a first exterior lateral wall, a second exterior lateral wall, an upper surface, a lower surface, a first interior lateral wall extending from the upper surface to the lower surface, a second interior lateral wall extending from the upper surface to the lower surface, an interior proximal wall extending from the upper surface to the lower surface and adjacent the first interior lateral wall and the second interior lateral wall, an interior distal wall extending from the upper surface to the lower surface and adjacent the first interior lateral wall and the second interior lateral wall, a longitudinal axis, and an interior cavity cooperatively defined by the interior proximal wall, the interior distal wall, the first interior lateral wall, and the second interior lateral wall, the interior proximal wall disposed on a first plane that is parallel to the longitudinal axis;
    the interior distal wall disposed on a second plane that is parallel to the longitudinal axis;
    the first interior lateral wall disposed on a third plane that is outwardly directed at a first angle from the lower surface to the upper surface relative to the longitudinal axis; and
    the second interior lateral wall disposed on a fourth plane that is outwardly directed at a second angle from the lower surface to the upper surface relative to the longitudinal axis.

2. The intervertebral spacer of claim 1, wherein the first exterior lateral wall is disposed on a fifth plane that is outwardly directed at a third angle from the lower surface to the upper surface relative to the longitudinal axis.

3. The intervertebral spacer of claim 2, wherein the second exterior lateral wall is disposed on a sixth plane that is outwardly directed at a fourth angle from the lower surface to the upper surface relative to the longitudinal axis.

4. The intervertebral spacer of claim 1, wherein the first exterior lateral wall defines an upper first exterior lateral wall portion and a lower first exterior lateral wall portion, the upper first exterior lateral wall portion extending from the upper surface toward the lower surface and the lower first exterior lateral wall portion disposed on a fifth plane that is outwardly directed at a third angle from the lower surface to the upper first exterior lateral wall portion relative to the longitudinal axis.

5. The intervertebral spacer of claim 4, wherein the second exterior lateral wall defines an upper second exterior lateral wall portion and a lower second exterior lateral wall portion, the upper second exterior lateral wall portion extending from the upper surface toward the lower surface and the lower second exterior lateral wall portion disposed on a sixth plane that is outwardly directed at a fourth angle from the lower surface to the upper second exterior lateral wall portion relative to the longitudinal axis.

6. The intervertebral spacer of claim 1, wherein the first angle is an angle between about 98° and about 117°.

7. The intervertebral spacer of claim 1, wherein the first angle is an angle between about 104° and about 111°.

8. The intervertebral spacer of claim 1, wherein the first angle is an angle between about 98° and about 117° and the second angle is an angle between about −98° and about −117°.

9. The intervertebral spacer of claim 1, wherein the first angle is an angle between about 104° and about 111° and the second angle is an angle between about −104° and about −111°.

10. The intervertebral spacer of claim 1, wherein the first angle is equal to the second angle.

11. The intervertebral spacer of claim 1, wherein the upper surface is rounded trapezoidal in shape.

12. The intervertebral spacer of claim 11, wherein the upper surface defines a first rounded trapezoidal opening to the interior cavity.

13. The intervertebral spacer of claim 12, wherein the lower surface is rounded trapezoidal in shape.

14. The intervertebral spacer of claim 13, wherein the lower surface defines a second rounded trapezoidal opening to the interior cavity.

15. The intervertebral spacer of claim 1, wherein the upper surface defines a first edge at which the upper surface is adjacent the interior proximal wall and each of the first interior lateral wall and the second interior lateral wall;
    wherein the first edge defines a first width extending from a first point disposed on the first edge and adjacent the first interior lateral wall to a second point disposed on the first edge and adjacent the second interior lateral wall;
    wherein the upper surface defines a second edge at which the upper surface is adjacent the interior distal wall and each of the first interior lateral wall and the second interior lateral wall;
    wherein the second edge defines a second width extending from a third point disposed on the second edge and adjacent the first interior lateral wall to a fourth point disposed on the second edge and adjacent the second interior lateral wall; and
    wherein the first width is greater than the second width.

16. An intervertebral spacer, comprising:
    a main body comprising an exterior proximal wall, an exterior distal wall, a first exterior lateral wall, a second exterior lateral wall, an upper surface, a lower surface, a first interior lateral wall extending from the upper surface to the lower surface, a second interior lateral wall extending from the upper surface to the lower surface, an interior proximal wall extending from the upper surface to the lower surface and adjacent the first interior lateral wall and the second interior lateral wall, an interior distal wall extending from the upper surface to the lower surface and adjacent the first interior lateral wall and the second interior lateral wall, a longitudinal axis, and an interior cavity cooperatively defined by the interior proximal wall, the interior distal wall, the first interior lateral wall, and the second interior lateral wall, the interior proximal wall disposed on a first plane that is parallel to the longitudinal axis;

the interior distal wall disposed on a second plane that is parallel to the longitudinal axis;

the first interior lateral wall disposed on a third plane that is outwardly directed at a first angle from the lower surface to the upper surface relative to the longitudinal axis;

the second interior lateral wall disposed on a fourth plane that is outwardly directed at a second angle from the lower surface to the upper surface relative to the longitudinal axis;

the first exterior lateral wall defining an upper first exterior lateral wall portion and a lower first exterior lateral wall portion, the upper first exterior lateral wall portion extending from the upper surface toward the lower surface and the lower first exterior lateral wall portion disposed on a fifth plane that is outwardly directed at a third angle from the lower surface to the upper first exterior lateral wall portion relative to the longitudinal axis; and the second exterior lateral wall defining an upper second exterior lateral wall portion and a lower second exterior lateral wall portion, the upper second exterior lateral wall portion extending from the upper surface toward the lower surface and the lower second exterior lateral wall portion disposed on a sixth plane that is outwardly directed at a fourth angle from the lower surface to the upper second exterior lateral wall portion relative to the longitudinal axis;

wherein the upper surface defines a first edge at which the upper surface is adjacent the interior proximal wall and each of the first interior lateral wall and the second interior lateral wall;

wherein the first edge defines a first width extending from a first point disposed on the first edge and adjacent the first interior lateral wall to a second point disposed on the first edge and adjacent the second interior lateral wall;

wherein the upper surface defines a second edge at which the upper surface is adjacent the interior distal wall and each of the first interior lateral wall and the second interior lateral wall;

wherein the second edge defines a second width extending from a third point disposed on the second edge and adjacent the first interior lateral wall to a fourth point disposed on the second edge and adjacent the second interior lateral wall; and wherein the first width is greater than the second width.

17. The intervertebral spacer of claim 16, wherein the upper surface is rounded trapezoidal in shape.

18. The intervertebral spacer of claim 17, wherein the lower surface is rounded trapezoidal in shape.

19. The intervertebral spacer of claim 18, wherein the upper surface defines a first rounded trapezoidal opening to the interior cavity and the lower surface defines a second rounded trapezoidal opening to the interior cavity.

20. An intervertebral spacer, comprising:

a main body comprising an exterior proximal wall, an exterior distal wall, a first exterior lateral wall, a second exterior lateral wall, an upper surface, a lower surface, a first interior lateral wall extending from the upper surface to the lower surface, a second interior lateral wall extending from the upper surface to the lower surface, an interior proximal wall extending from the upper surface to the lower surface and adjacent the first interior lateral wall and the second interior lateral wall, an interior distal wall extending from the upper surface to the lower surface and adjacent the first interior lateral wall and the second interior lateral wall, a longitudinal axis, and an interior cavity cooperatively defined by the interior proximal wall, the interior distal wall, the first interior lateral wall, and the second interior lateral wall;

the interior proximal wall disposed on a first plane that is parallel to the longitudinal axis;

the interior distal wall disposed on a second plane that is parallel to the longitudinal axis;

the first exterior lateral wall being disposed on a third plane that is outwardly directed at a first angle from the lower surface to the upper surface relative to the longitudinal axis, the first interior lateral wall being disposed on a fourth plane that is outwardly directed at a second angle from the lower surface to the upper surface relative to the longitudinal axis.

* * * * *